United States Patent
Miao et al.

(10) Patent No.: US 12,194,032 B2
(45) Date of Patent: *Jan. 14, 2025

(54) METHOD OF TREATING FOCAL SEGMENTAL GLOMERULOSCLEROSIS

(71) Applicant: ChemoCentryx, Inc., San Carlos, CA (US)

(72) Inventors: Zhenhua Miao, San Carlos, CA (US); Thomas Schall, San Carlos, CA (US); Rajinder Singh, San Carlos, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 17/658,494

(22) Filed: Apr. 8, 2022

(65) Prior Publication Data

US 2022/0226294 A1 Jul. 21, 2022

Related U.S. Application Data

(63) Continuation of application No. 16/946,402, filed on Jun. 19, 2020, now Pat. No. 11,324,736, which is a continuation of application No. 15/821,490, filed on Nov. 22, 2017, now Pat. No. 10,973,809.

(60) Provisional application No. 62/425,832, filed on Nov. 23, 2016.

(51) Int. Cl.
| | |
|---|---|
| *A61K 31/444* | (2006.01) |
| *A61K 31/137* | (2006.01) |
| *A61K 31/28* | (2006.01) |
| *A61K 31/403* | (2006.01) |
| *A61K 31/4178* | (2006.01) |
| *A61K 31/4184* | (2006.01) |
| *A61K 31/426* | (2006.01) |
| *A61K 31/44* | (2006.01) |
| *A61K 31/4418* | (2006.01) |
| *A61K 31/4422* | (2006.01) |
| *A61K 31/519* | (2006.01) |
| *A61K 31/7034* | (2006.01) |
| *A61K 35/545* | (2015.01) |
| *A61K 39/395* | (2006.01) |
| *A61P 13/12* | (2006.01) |

(52) U.S. Cl.
CPC ......... *A61K 31/444* (2013.01); *A61K 31/137* (2013.01); *A61K 31/28* (2013.01); *A61K 31/403* (2013.01); *A61K 31/4178* (2013.01); *A61K 31/4184* (2013.01); *A61K 31/426* (2013.01); *A61K 31/44* (2013.01); *A61K 31/4418* (2013.01); *A61K 31/4422* (2013.01); *A61K 31/519* (2013.01); *A61K 31/7034* (2013.01); *A61K 35/545* (2013.01); *A61K 39/3955* (2013.01); *A61P 13/12* (2018.01)

(58) Field of Classification Search
CPC .................................................... A61K 31/444
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,901,855 | A | 8/1975 | Arnold |
| 3,939,350 | A | 2/1976 | Kronick et al. |
| 3,996,345 | A | 12/1976 | Ullman et al. |
| 4,166,452 | A | 9/1979 | Generales, Jr. |
| 4,227,437 | A | 10/1980 | Inloes et al. |
| 4,256,108 | A | 3/1981 | Theeuwes |
| 4,265,874 | A | 5/1981 | Bonsen et al. |
| 4,275,149 | A | 6/1981 | Litman et al. |
| 4,277,437 | A | 7/1981 | Maggio |
| 4,366,241 | A | 12/1982 | Tom et al. |
| 4,403,607 | A | 9/1983 | Woo et al. |
| 5,120,643 | A | 6/1992 | Ching et al. |
| 5,292,758 | A | 3/1994 | Yoshino et al. |
| 5,446,139 | A | 8/1995 | Seela et al. |
| 5,571,775 | A | 11/1996 | Van Heertum et al. |
| 5,780,488 | A | 7/1998 | Bergman et al. |
| 5,973,148 | A | 10/1999 | Ringer et al. |
| 5,990,479 | A | 11/1999 | Weiss et al. |
| 6,207,392 | B1 | 3/2001 | Weiss et al. |
| 6,251,303 | B1 | 6/2001 | Bawendi et al. |
| 6,306,610 | B1 | 10/2001 | Bawendi et al. |
| 6,312,914 | B1 | 11/2001 | Kardos et al. |
| 6,319,426 | B1 | 11/2001 | Bawendi et al. |

(Continued)

FOREIGN PATENT DOCUMENTS

| | | |
|---|---|---|
| CN | 103476410 B | 2/2020 |
| DE | 3825041 A1 | 2/1990 |

(Continued)

OTHER PUBLICATIONS

CAS Registry No. 1100318-47-5 ; STN Entry Date Feb. 3, 2009; Benzenesulfonamide, 4-chloro-N-[5-methyl-2-(7H-pyrrolo[2,3-d]pyrimidin-4-ylcarbonyl)-3-pyridinyl]-3-(trifluoromethyl)-.
IP Australia; Application No. 2017363299; Notice of Acceptance mailed Dec. 12, 2022. 3 pages.
IP Australia; Application No. 2017363299; Reissued Notice of Acceptance mailed Feb. 21, 2023. 4 pages.
De Zeeuw, D. D. et al. "CCR2 Inhibitor CCX140 Effective In Phase 2 Clinical Trial In Diabetic Nephropathy" Nephrology Dialysis TRansplantation (2015) vol. 30, ii531-ii536, abstract SP 457.
Vande Broek, et al., "Chemokine receptor CCR2 is expressed by human multiple myeloma cells and mediates migration to bone marrow stromal cell-produced monocyte chemotactic proteins MCP-1, -2 and -3", British Journal of Cancer, 88:855-862 (2003).

(Continued)

*Primary Examiner* — Rei Tsang Shiao
(74) *Attorney, Agent, or Firm* — Robert Bernstein

(57) ABSTRACT

A method of treating focal segmental glomerulosclerosis with a compound of Formula I is provided. FSGS may be primary (no known cause) or secondary. The secondary FSGS may be associated with infections or viruses such as HIV, diseases such as sickle cell disease or lupus, toxins or drugs such as anabolic steroids, heroin or pamidronate, nephron loss and hyperfiltration, such as with chronic pyelonephritis and reflux, morbid obesity, or diabetes mellitus.

20 Claims, 8 Drawing Sheets

(56) References Cited

U.S. PATENT DOCUMENTS

| | | | |
|---|---|---|---|
| 6,322,901 B1 | 11/2001 | Bawendi et al. | |
| 6,326,144 B1 | 12/2001 | Bawendi et al. | |
| 6,380,206 B1 | 4/2002 | Pamukcu et al. | |
| 6,403,607 B1 | 6/2002 | Hidaka et al. | |
| 6,423,551 B1 | 7/2002 | Weiss et al. | |
| 6,444,143 B2 | 9/2002 | Bawendi et al. | |
| 6,451,339 B2 | 9/2002 | Patel et al. | |
| 6,479,527 B1 | 11/2002 | Barker et al. | |
| 6,489,452 B1 | 12/2002 | Tateishi et al. | |
| 6,939,885 B2 | 9/2005 | Ungashe et al. | |
| 7,282,502 B2 | 10/2007 | Fleming et al. | |
| 7,496,807 B2 | 2/2009 | Nagai et al. | |
| 7,622,583 B2 | 11/2009 | Ungashe et al. | |
| 7,884,110 B2 | 2/2011 | Krasinski et al. | |
| 8,093,247 B2 | 1/2012 | Ungashe et al. | |
| 8,519,135 B2 | 8/2013 | Chen et al. | |
| 8,546,408 B2 | 10/2013 | Krasinski et al. | |
| 9,394,307 B2 | 7/2016 | Krasinski et al. | |
| 9,745,312 B2 | 8/2017 | Krasinski et al. | |
| 10,758,540 B2 * | 9/2020 | Miao | A61K 31/437 |
| 10,973,809 B2 * | 4/2021 | Miao | A61K 39/3955 |
| 11,324,736 B2 * | 5/2022 | Miao | A61K 31/137 |
| 11,382,915 B2 * | 7/2022 | Miao | A61K 31/422 |
| 2002/0052363 A1 | 5/2002 | Dinsmore et al. | |
| 2002/0103202 A1 | 8/2002 | Pinto et al. | |
| 2003/0229081 A1 | 12/2003 | Maduskuie | |
| 2004/0023286 A1 | 2/2004 | Wei | |
| 2004/0038976 A1 | 2/2004 | Fleming et al. | |
| 2004/0106613 A1 | 6/2004 | McNaughton-Smith et al. | |
| 2004/0171654 A1 | 9/2004 | Ugashe et al. | |
| 2006/0111351 A1 | 5/2006 | Ungashe et al. | |
| 2006/0173019 A1 | 8/2006 | Ungashe et al. | |
| 2007/0021466 A1 | 1/2007 | Ungashe et al. | |
| 2007/0037794 A1 | 2/2007 | Ungashe et al. | |
| 2007/0219245 A1 | 9/2007 | Hou et al. | |
| 2009/0197884 A1 | 8/2009 | Ghosh et al. | |
| 2010/0056509 A1 | 3/2010 | Ungashe et al. | |
| 2010/0234364 A1 | 9/2010 | Basak et al. | |
| 2010/0249118 A1 | 9/2010 | Ibrahim et al. | |
| 2011/0118248 A1 | 5/2011 | Ungashe et al. | |
| 2011/0274696 A1 | 11/2011 | Gladue et al. | |
| 2011/0319433 A1 | 12/2011 | Krasinski et al. | |
| 2012/0122860 A1 | 5/2012 | Visor et al. | |
| 2014/0031348 A1 | 1/2014 | Ungashe et al. | |
| 2014/0100237 A1 | 4/2014 | Krasinski et al. | |
| 2014/0235661 A1 | 8/2014 | Ebel et al. | |
| 2015/0080351 A1 | 3/2015 | Ungashe et al. | |
| 2017/0095458 A1 | 4/2017 | Ungashe et al. | |
| 2017/0334920 A1 | 11/2017 | Krasinski et al. | |
| 2017/0368043 A1 | 12/2017 | Bekker et al. | |

FOREIGN PATENT DOCUMENTS

| | | |
|---|---|---|
| EP | 0472053 B1 | 6/1998 |
| EP | 0937711 A1 | 8/1999 |
| EP | 1334719 A2 | 8/2003 |
| JP | S61113060 A | 5/1986 |
| JP | 2000159665 A | 6/2000 |
| JP | 2001089412 A | 4/2001 |
| JP | 2003040726 A | 2/2003 |
| JP | 4364168 B2 | 11/2009 |
| JP | 6135934 B2 | 5/2017 |
| JP | 6145145 B2 | 6/2017 |
| WO | 1994020142 A1 | 9/1994 |
| WO | 1998011218 A1 | 3/1998 |
| WO | 1999042439 A1 | 8/1999 |
| WO | 2000040560 A1 | 7/2000 |
| WO | 2001000611 A1 | 1/2001 |
| WO | 2001002369 A2 | 1/2001 |
| WO | 2001072744 A1 | 10/2001 |
| WO | 2002101350 A2 | 12/2002 |
| WO | 2003032994 A2 | 4/2003 |
| WO | 2003051870 A1 | 6/2003 |
| WO | 2003099773 A1 | 12/2003 |
| WO | 2004046092 A2 | 6/2004 |
| WO | 2004056774 A2 | 7/2004 |
| WO | 2004058164 A2 | 7/2004 |
| WO | 2004058265 A1 | 7/2004 |
| WO | 2004085384 A2 | 10/2004 |
| WO | 2004099127 A1 | 11/2004 |
| WO | 2004105794 A2 | 12/2004 |
| WO | 2005004810 A2 | 1/2005 |
| WO | 2005028445 A2 | 3/2005 |
| WO | 2005112916 A2 | 12/2005 |
| WO | 2005112925 A1 | 12/2005 |
| WO | 2006029173 A2 | 3/2006 |
| WO | 2006076644 A2 | 7/2006 |
| WO | 2007014008 A2 | 2/2007 |
| WO | 2007014054 A2 | 2/2007 |
| WO | 2008008374 A2 | 1/2008 |
| WO | 2008008394 A1 | 1/2008 |
| WO | 2008008431 A2 | 1/2008 |
| WO | 2009009740 A1 | 1/2009 |
| WO | 2012041817 A1 | 4/2012 |
| WO | 2015062743 A1 | 5/2015 |

OTHER PUBLICATIONS

VanRiper, et al., "Characterization and Species Distribution of High Affinity GTP-coupled Receptors for Human Rantes and Monocyte Chemoattractant Protein 1", J. Exp. Med., 177:851-856 (Mar. 1993).

Vervoordeldonk, et al., "Cytokines in Rheumatoid Arthritis", Current Rheumatology Reports, 4:208-217 (2002).

Vestergaard, et al., "Expression of CCR2 on Monocytes and Macrophages in Chronically Inflamed Skin in Atopic Dermatitis and Psoriasis", Acta. Derm. Venereal., 84(5):353-358 (2004).

Villiger, et al., "Production of Monocyte Chemoattractant Protein-1 by Inflamed Synovial Tissue and Cultured Synoviocytes", J Immunol., 149(2):722-727 (1992).

Weisberg, et al., "CCR2 modulates inflammatory and metabolic effects of high-fat feeding", The Journal of Clinical Investigation, 116(1):115-124 (Jan. 2006).

Weisberg, et al., "Obesity is associated with macrophage accumulation in adipose tissue", J Clin. Invest., 112(12):1796-1808 (2003).

Wurbel, et al., "Mice lacking the CCR9 CC-chemokine receptor show a mile impairment of early T-and B-cell development and a reduction in T-cell receptor y +", Blood, 98(9):2626-2632 (2001).

Xu, et al., "Chronic inflammation in fat plays a crucial role in the development of obesity-related insulin resistance", J Clin. Invest., 112(12):1821-1830 (2003).

Yang, et al., "Phenotypic Characteristics of infiltrated inflammatory cells, renal tubular epithelial cells and interstitial cells and their possible roles in the outcome of human drug-associated interstitial nephritis", National Medical Journal of China, 81(2):73-77 (Jan. 2001).

Yogi, Seiichi, et al., "Synthesis of imido-substituted 3,8-diphenyl-1,2-diazacycloocta-2,4,6,8-tetraenes and their thermolysis," Bull. Chem. Soc. Jpn., 60:731-735 (1987).

Yoshimatsu, K., et al. "Mechanism of action of E7010, an orally active sulfonamide antitumor agent: Inhibition of mitosis by binding to the clochicine site of tubulin," Cancer Research, 57(15):3208-3218 (1997).

Yoshino, et al., "Novel Sulfonamides as Potential, Systemically Active Antitumor Agents", J. Med. Chem., 35:2496-2497 (1992).

Youn, et al., "Role of the CC Chemokine receptor 9/TECK interaction in apoptosis", Apoptosis, 7(3):271-276 (2002).

Zaballos, et al., "Cutting Edge: Identification of the Orphan Chemokine Receptor CPR-9-6 as CCR9, the Receptor for the Chemokine TECK," J. Immunol., 162:5671-5675 (1999).

Chemocentryx Press Release, https://ir.chemocentryx.com/news-releases/news-release-details/chemocentryx-and-vfmcrp-announce-topline-data-phase-ii-lumina-1, dated May 18, 2020.

Miao, Zhenhua, et al. "TO041 CCR2 Antagonism Reduces Proteinuria and Glomerular Injury in Murine Models of Focal Segmental Glomerulosclerosis (FSGS)", Nephrology Dialysis Transplantation., 32(3):pp. iii97-iii97, doi:10.1093/ndt/gfx134.

(56) References Cited

OTHER PUBLICATIONS

Amann, et al., "ACE Inhibitors Improve Diabetic Nephropathy Through Suppression of Renal MCP-1", Diabetes Care, 26(8):2421-2425 (Aug. 2003).
Babu, et al., "Chemokine Receptors of T Cells and of B Cells in Lymphatic Filarial Infection: A Role for CCR9 in Pathogenesis," Journal of Infectious Diseases, 191:1018-1026 (2005).
Baker, B.R., et al., "Puromycin. Synthetic studies. II. The position of glycosidation on the 6-dimethylaminopurine moiety," J. Org. Chem., 19:638-645 (1954).
Beilstein Data XP002464251 BRN:7928945 (2000).
Beilstein Data XP002464252 BRN:7313089 (1995).
Beilstein Data XP002464253 BRN:329227 (1949).
Beilstein Data XP002464254 BRN:7102156 (1987).
Beilstein Data XP002464255 BRN:6875780 (1983).
Bendele, et al., "Animal Models of Arthritis: Relevance to Human Disease," Toxicologic Pathology, 27(1):134-142 (1999).
Bendele, et al., "Efficacy of Sustained Blood Levels of Interleukin-1 Receptor Antagonist in Animal Models of Arthritis," Arthritis & Rheum., 42(3):498-506 (1999).
Berge, Stephen M., et al., "Pharmaceutical Salts," J. Pharm. Sci., 66(1):1-19 (Jan. 1977).
Berman, et al., "Lymphocyte Motility and Lymphocyte Chemoattractant Factors", Immunol. Invest., 17:625-677, 1988.
Bredereck, Hellmutt, et al., "Synthesen in der Purinreihe. XVI. Uber die Darstellung von 5-Alkyl-bzw.5-Arylsulfonylamino-4-aminouracilen, 4-Amino-5-alkylamino-uracilen und 4-Amino-5-[pyridiniomethylenamino]-uracil-chloriden," Chemische Berichte, 95:1902-1909 (1962).
Broek, I. Vande, et al., "Chemokine receptor CCR2 is expressed by human multiple myeloma cells and mediates migration to bone marrow stromal cell-produced monocyte chemotactic proteins MCP-1, -2 and -3," Br. J. Cancer, 88(6):855-862 (2003).
Campbell, et al., "Rapid Acquisition of Tissue-specific Homing Phenotypes by CD4+T Cells Activated in Cutaneous or Mucosal Lymphoid Tissues", J. Exp. Med., 195(1):135-141 (2002).
Charo, I., et al., CCX872-B: Pharmacodynamic Study of a Potent and Selective CCR2 Antagonist in Human Volunteers and Clinical Trial Design in Patients with Pancreatic Cancer, ChemoCentryx Poster CT223, 1 page (Apr. 2015).
ChemoCentryx, "ChemoCentryx Announces Immuno-Oncology Data Presentations at the AACR-NCI-EORTC Molecular Targets and Cancer Therapeutics Meeting," 3 pages (Nov. 4, 2015).
ChemoCentryx, "ChemoCentryx Initiates Clinical Trial of CCX872, Its Next-Generation, Orally Administered CCR2 Inhibitor, in Pancreatic Cancer," 3 pages (Apr. 20, 2015).
ChemoCentryx, "ChemoCentryx Reports First Quarter 2015 Financial Results and Provides Corporate Update," 5 pages (May 6, 2015).
ChemoCentryx, "ChemoCentryx Reports Fourth Quarter 2014 Financial Results and Provides Corporate Update," 5 pages (Mar. 12, 2015).
ChemoCentryx, "ChemoCentryx Reports Second Quarter 2015 Financial Results and Provides Corporate Update," 5 pages (Aug. 6, 2015).
ChemoCentryx, "ChemoCentryx Reports Third Quarter 2014 Financial Results and Provides Corporate Update," 5 pages (Nov. 5, 2014).
ChemoCentryx, "ChemoCentryx Reports Third Quarter 2015 Financial Results and Provides Corporate Update," 5 pages (Nov. 9, 2015).
ChemoCentryx, "ChemoCentryx to Hold First Quarter 2015 Financial Results Conference Call on Wednesday, May 6, 2015," 2 pages (Apr. 22, 2015).
ChemoCentryx, "ChemoCentryx to Hold Second Quarter 2015 Financial Results Conference Call on Thursday, Aug. 6, 2015," 2 pages (Jul. 29, 2015).
ChemoCentryx, "ChemoCentryx to Hold Third Quarter 2015 Financial Results Conference Call on Monday, Nov. 9, 2015," 2 pages (Oct. 29, 2015).
ChemoCentryx, "ChemoCentryx to Present at the Rodman & Renshaw 17th Annual Global Investment Conference," 2 pages (Sep. 2, 2015).
ChemoCentryx, "ChemoCentryx to Present at Two Upcoming Investor Conferences," 2 pages (May 12, 2015).
ChemoCentryx, "ChemoCentryx to Present at Two Upcoming Investor Conferences," 2 pages (Nov. 12, 2015).
Christiansen, et al., "Monocyte chemoattractant protein-1 is produced in isolated adipocytes, associated with adiposity and reduced after weight loss in morbid obese subjects", International Journal of Obesity, 29:146-150 (2005).
Dahinden, et al., "Monocyte Chemotactic Protein 3 Is a Most Effective Basophil- and Eosinophil-activating Chemokine", J. Exp. Med., 179:751-756 (1994).
Dai, et al., "Monocyte chemoattractant protein-1 expression in renal tissue is associated with monocyte recruitment and tubule-interstitial lesions in patients with lupus nephritis", Chinese Medical Journal, 114(8):864-868 (2001).
Davidson, et al., "T Helper Cell 1-type CD4+T Cells, but Not B Cells, Mediate Colitis in Interleukin 10-deficient Mice", J. Exp. Med., 184:241-251 (1996).
De Mik, SM, et al., "Pathophysiology and treatment of focal segmental glomerulosclerosis: the role of animal models," BMC Nephrol. 14:74 (Apr. 1, 2013).
Deleuran, et al, "Localization of monocyte chemotactic and activating factor (MCAF/MCP-1) in psoriasis", Journal of Dermatological Science, 13:228-236 (1996).
De Zeeuw, Dick et al. "The effect of CCR2 inhibitor CCX140-B on residual albuminuria in patients with type 2 diabetes and nephropathy: a randomised trial." The lancet. Diabetes & endocrinology vol. 3,9 (2015): 687-96. doi:10.1016/S2213-8587(15)00261-2.
Diamond, et al., "Macrophages, monocyte chemoattractant peptide-1, and TGF-.beta. 1 in experimental hydronephrosis", American Journal of Physiology, 226(6):F926-F933 (Jun. 1994).
Dorwald, "Side Reactions in Organic Synthesis: A Guide to Successful Synthesis Design" Wiley-VCH Verlag GmbH & KGaA, Weinheim, Preface (2005).
Eddy, et al., "Renal expression of genes that promote interstitial inflammation and fibrosis in rats with protein-overload proteinuria", Kidney International, 47:1546-1557 (1995).
Ellingson, et al. "Pyrazine chemistry. III. Derivatives of 3-amino-5,6-dimethylpyrazineie acid," J. Am. Chem. Soc., 70:1257-1261 (1948).
El-Subbagh, et al., "Novel diarylsulphide derivatives as potential cytotoxic agents", Bollettino Chimico Farmaceutico, 134:80-84 (1995).
Eskens, Ferry, et al., "Pharmacokinetic and Pharmacodynamic Profile of the Novel, Oral and Selective CCR2 Inhibitor CCX872-B in a Phase 1B Pancreatic Cancer Trial," ChemoCentryx Poster IBCD15-020, 1 page, (Dec. 2015).
Feria, Manuel, et al., "The CCR2 receptor as a therapeutic target," Expert Opinion on Therapeutic Patents, Informa Healthcare, GB, 16(1):49-57 (2006).
Gillitzer, et al., "MCP-1 mRNA Expression in Basal Keratinocytes of Psoriatic Lesions", J. InvestDermatol, 101:127-131 (1993).
Gong, et al., "An Antagonist of Monocyte Chemoattractant Protein 1 (MCP-1) Inhibits Arthritis in the MRL-Ipr Mouse Model", J. Exp. Med., 186(1):131-137 (Jul. 1997).
Gonzales-Cuadrado, et al., "Expression of leucocyte chemoattractants by interstitial renal fibroblasts: up-regulation by drugs associated with interstitial fibrosis", Clin. Exp. Immunol., 106:518-522 (1996).
Hezel, Aram, et al., "Pharmacokinetic and Pharmacodynamic Profile of a Novel Orally-administered CCR2 Inhibitor, CCX872-B, in a Pancreatic Cancer Trial," ChemoCentryx Poster B24, 1 page (Nov. 2015).
International Search Report and Written Opinion for corresponding International Application No. PCT/US2017/063120, 11 pages (Mar. 8, 2018).
International Search Report and Written Opinion for International Application No. PCT/US2017/035628 (Aug. 29, 2017).
International Search Report and Written Opinion for International Application No. PCT/US2017/037264 (Oct. 6, 2017).

(56) References Cited

OTHER PUBLICATIONS

International Search Report for International Application No. PCT/US2007/015893 (Jan. 22, 2008).
International Search Report for International Application No. PCT/US2007/015785 (Oct. 23, 2008).
Kavanaugh, et al., "Role of CD11/CD18 in Adhesion and Transendothelial Migration of T Cells", J. Immunol., 146:4149-4156 (Jun. 1991).
Kitagawa, et al., "Blockade of CCR2 Ameliorates Progressive Fibrosis in Kidney", American Journal of Pathology, 165(1):237-246 (Jul. 2004).
Kontoyiannis et al., "Impaired On/Off Regulation of TNF Biosynthesis in Mice Lacking TNF AU-Rich Elements: Implications for Joint and Gut-Associated Immunopathologies", Immunity, 10:387-398 (Mar. 1999).
Kontoyiannis, et al., "Genetic Dissection of the Cellular Pathways and Signaling Mechanisms in Modeled Tumor Necrosis Factor-induced Crohn's-like Inflammatory Bowel Disease," J. Exp. Med., 196(2):1563-1574 (2002).
Kosiewicz, et al., "Th1-type responses mediate spontaneous ileitis in a novel murine model of Crohn's disease", J. Clin. Invest., 107(6):695-702 (Mar. 2001).
Kunkel, et al., "Lymphocyte CC Chemokine Receptor 9 and Epithelial Thymus-expressed Chemokine (TECK) Expression Distinguish the Small Intestinal Immune Compartment: Epithelial Expression of Tissue-specific Chemokines as an Organizing Principle in Regional Immunity", J. Exp. Med., 192(5):761-777 (Sep. 2000).
Kuse, Masaki, et al., "Novel synthetic route of aryl-aminopyrazine," Tetrahedron, 60:835-840 (2004).
Lloyd, et al., "RANTES and Monocyte Chemoattractant Protein-1 (MCP-1) Play an Important Role in the Inflammatory Phase of Crescentic Nephritis, but Only MCP-1 Is Involved in Crescent Formation and Interstitial Fibrosis", J. Exp. Med., 185(7):1371-1380 (Apr. 1997).
Martins, et al., "Nanoparticle Drug Delivery Systems: Recent Patents and Applications in Nanomedicine," Recent Patents on Nanomedicine, 3(2):105-118 (2013).
McDonald, Francis G., et al., "Pyrazine Chemistry. II. Derivatives of 3-Hydroxypyrazinoic Acid," J. Am. Chem. Soc., 69(5):1034-1037 (1947).
Mine, et al., "Increased expression levels of monocyte CCR2 and monocyte chemoattractant protein-1 in patients with diabetes mellitus", Biochemical and Biophysical Research Comm., 334:780-785 (2006).
Morii, et al., "Association of monocyte chemoattractant protein-1 with renal tubular damage in diabetic nephropathy", Journal of Diabetes Complications, 17:11-15 (2003).
Murphy, "The Molecular Biology of Leukocyte Chemoattractant Receptors", Ann. Rev. Immun., 12:593-633 (1994).
National Kidney Foundation, "Focal Segmental Glomerulosclerosis (FSGS)", https://www.kidney.org/atoz/content/focal (accessed Mar. 27, 2019) (Year: 2019).
Neote, et al., "Molecular Cloning, Functional Expression, and Signaling characteristics of a C—C Chemokine Receptor", Cell, 72:415-425 (Feb. 1993).
Ogata, et al., "The Role of Monocyte Chemoattractant Protein-1 (MCP-1) in the Pathogenesis of Collagen-Induced Arthritis in Rats", Journal of Pathology, 182:106-114 (1997).
Panwala, et al., "A Novel Model of Inflammatory Bowel Disease: Mice Deficient for the Multiple Drug Resistance Gene, mdrla, Spontaneously Develop Colitis", J. Immunol., 161:5733-5744 (1998).
Papadakis, et al., "The Role of Thymus-Expressed Chemokine and Its Receptor CCR9 on Lymphocytes in the Regional Specialization of the Mucosal Immune System", J. Immunol., 165:5069-5076 (2000).
Papadikis, et al., "CCR9-Positive Lymphocytes and Thymus-Expressed Chemokine Distinguish Small Bowel from Colonic Crohn's Disease," Gastroenterology, 121(2):248-254 (2001).

Plater-Zyberk, et al., "Effect of a CC chemokine receptor antagonist on collagen induced arthritis in DBA/1 mice", Immunology Letters, 57:117-120 (1997).
Powrie et al., "Phenotypically distinct subsets of CD4+ T cells induce or protect from chronic intestinal inflammation in C. B-17 scid mice", Int. Immunol., 5(11):1461-1471 (1993).
Qiuping, et al., "Selectively Increased Expression and Functions of Chemokine Receptor CCR9 on CD4+ T Cells from Patients with T-Cell Lineage Acute Lymphocytic Leukemia", Cancer Res., 63:6469-6477 (Oct. 2003).
Rivera-Nieves, et al., "Antibody Blockade of CCL25/CCR9 Ameliorates Early but not Late Chronic Murine Ileitis," Gastroenterology, 131(5):1518-1529 (2006).
Sartipy, et al., "Monocyte chemoattractant protein 1 in obesity and insulin resistance", PNAS, 100(12):7265-7270 (Jun. 2003).
Sayyed SG, Ryu M, Kulkarni OP, Schmid H, Lichtnekert J, Gruner S, Green L, Mattei P, Hartmann G, Anders HJ. "An orally active chemokine receptor CCR2 antagonist prevents glomerulosclerosis and renal failure in type 2 diabetes" Kidney Int vol. 80, pp. 68-78, 2011 (Year: 2011).
Scaife, et al., "Detection of differentially expressed genes in synovial fibroblasts by restriction fragment differential display", Rheumatology, 43(11):1346-1352 (Aug. 2004).
Schall, "Biology of the Rantes/sis Cytokine Family", Cytokine, 3(3):165-183 (May 1991).
Schall, et al., "Chemokines, leukocyte trafficking, and inflammation", Curr. Opin, Immunol., 6:865-873 (1994).
Science IP Search Results (Dec. 16, 2004).
Science IP Search Results (Mar. 29, 2006).
SCIFINDER Search Results (Jan. 24, 2006)—ether linker.
SCIFINDER Search Results (Jan. 24, 2006)—keto linker.
Segerer, et al., "Chemokines, Chemokine Receptors, and Renal Disease: From Basic Science to Pathophysiologic and Therapeutic Studies", J. Am. Soc. Nephrol., 11:152-176 (2000).
Sell, et al., "Monocyte Chemotactic Protein-1 Is a Potential Player in the Negative Cross-Talk between Adipose Tissue and Skeletal Muscle", Endocrinology, pp. 2458-2467 (2006).
Shadidi, et al., "The Chemokines CCL5, CCL2 and CXCL12 Play Significant Roles in the Migration of Th1 Cells into Rheumatoid Synovial Tissue", Scandinavia Journal of/mmunology, 57:192-198 (2003).
Shimizu, et al., "Anti-Monocyte Chemoattractant Protein-1 Gene Therapy Attenuates Renal Injury Inducted by Protein-Overload Proteinuria", J. Am. Soc. Nephrol., 14:1496-1505 (2003).
Sprecher, et al., "Methylated purines and pyrimidines, II Synthesis and properties 2,6-diamino-5-(methylamino)-4-pyrimidinol," Biochemistry, 4(4):655-661 (1965).
Stephan, et al., "Urinary Concentration and Tissue Messenger RNA Expression of Monocyte Chemoattractant Protein-1 As An Indicator of the Degree of Hydronephrotic Atrophy in Partial Ureteral Obstruction", The Journal of Urology, 167:1497-1502 (Mar. 2002).
Takahashi, et al., "Adiposity Elevates Plasma MCP-1 Levels Leading to the Increased CD11b-positive Monocytes in Mice", The Journal of Biological Chemistry, 278(47):46654-46660 (Nov. 2003).
Targan, et al., "A Short-Term Study of Chimeric Monoclonal Antibody cA2 To Tumor Necrosis Factor .alpha. for Crohn's Disease", N. Engl. J. Med., 337(15):1029-1035 (1997).
Taylor, et al., "Reduction of Chemokine Levels and Leukocyte Traffic to Joints by Tumor Necrosis Factor .alpha. Blockade in Patients with Rheumatoid Arthritis," Arthritis & Rheumatism, 43(1):38-47 (Jan. 2000).
Tedder et al., "Structure-based design, synthesis, and antimicrobial activity of purine derived SAH/MTA nucleosidase inhibitors", Bioorganic & Medicinal Chemistry Letters, 14:3165-3168 (2004).
Trentham, et al., "Autoimmunity to Type II Collagen: An Experimental Model of Arthritis," J. Exp. Med., 146:857-868 (1977).
Tsuge, O., et al., "Synthesis of Imido-Substituted 3,8-Diphenyl-1,2-diazacycloocta- 2,4,6,8-tetraenes and Their Thermolysis," Bull Chem. Soc. Jpn. 60:731-735 (1987).
Tucci, et al., "Synovial Tissues Collected from Rheumatoid Patients Undergoing Total Joint Arthroplasty Express Markers for Acute Inflammation", Biomedical Sciences Instrumentation, 34:169-174 (1997).

(56) References Cited

OTHER PUBLICATIONS

Tu Yuanmao et al., "Current treatment of focal segmental glomerulosclerosis", J Nephrol Dialy Transplant, vol. 23, No. 4 (2014).

Uehara, et al., "A Role for CCR9 in T Lymphocyte Development and Migration", J. Immunol., 168(6):2811-2819 (2002).

Ueno, et al., "Significance of Macrophase Chemoattractant Protein-1 in Macrophage Recruitment, Angiogenesis, and Survival in Human Breast Cancer", Clinical Cancer Research, 6:3282-3289 (Aug. 2000).

Garde, Damian, "ChemoCentryx Announces Positive Results in Phase II Diabetic Nephropathy Trial With CCR2 Inhibitor CCX140," Fierce Biotech, Dec. 12, 2014.

CCX-140, PubChem CID 163321464, National Library of Medicine, Deposited May 30, 2013, Modified Jul. 27, 2021, Available May 30, 2013.

\* cited by examiner

Control (No drug)

Compound 3

METHOD OF TREATING FOCAL SEGMENTAL GLOMERULOSCLEROSIS

This application is a continuation of U.S. patent application Ser. No. 16/946,402, filed Jun. 19, 2020, which is a continuation of U.S. patent application Ser. No. 15/821,490, filed Nov. 22, 2017, which claims priority to U.S. Provisional Application No. 62/425,832, filed Nov. 23, 2016. The disclosure of these priority applications are incorporated by reference herein in their entirety.

FIELD

The present disclosure describes methods of treating focal segmental glomerulosclerosis (FSGS) with a compound of Formula I. FSGS comprises a group of disorders characterized renal lesions that appear on light microscopy to involve only some (focal) glomeruli and only part (segmental) of involved glomeruli. FSGS may occur in the context of genetic risk factors (genetic FSGS), heterozygosity or homozygosity for risk variants of apoL1 (apoL1 FSGS), exposure to viruses (viral FSGS), increased filtration demand on nephrons (adaptive FSGS, as may occur in the setting of nephron loss, hypertension, obesity, other conditions), exposure to toxins or medications (toxic FSGS), in the context of other renal or systemic diseases (secondary FSGS, as may occur in the setting of diabetes, lupus nephritis, and other diseases), in the context of recognized or unrecognized circulation factors or may be idiopathic (primary FSGS).

FSGS may be primary (no known cause) or secondary. The secondary FSGS may be associated with infections or viruses such as HIV, diseases such as sickle cell disease or lupus, toxins or drugs such as anabolic steroids, heroin or pamidronate, nephron loss and hyperfiltration, such as with chronic pyelonephritis and reflux, morbid obesity, or diabetes mellitus.

BACKGROUND

FSGS is used to describe both a disease characterized by primary podocyte injury, and a lesion that occurs secondarily in any type of chronic kidney disease (CKD). It is defined by the presence of sclerosis in parts (segmental) or some glomeruli (focal) by light microscopy. FSGS can be found without an identifiable cause ("primary" or "idiopathic" FSGS represents 80% of cases) or in response to previous glomeruli injury, such as hypertension or obesity ("secondary" FSGS represents 20% of cases).

The most common manifestation of FSGS is proteinuria ranging from subnephrotic to nephrotic levels (heavy proteinuria, hypoalbuminemia and hyperlipidemia). Heavy proteinuria leads to progressive loss of kidney function (glomerulosclerosis) and kidney failure. It accounts for ~15% of end-stage renal disease (ESRD). Massive proteinuria (>10-15 g/day) leads to rapid deterioration of renal function and progression to ESRD within 2-3 years. The survival rate of FSGS patients with massive proteinuria is only 45%.

Focal segmental glomerulosclerosis is listed as a "rare disease" by the Office of Rare Diseases (ORD) of the National Institutes of Health (NIH) and there is no current approved drug for FSGS. About 5400 patients are diagnosed with FSGS every year in the United States, but the number of cases is rising more than any other cause of Nephrotic Syndrome. Approximately 1,000 FSGS patients receive kidney transplants every year. Within hours to weeks after a kidney transplant, however, FSGS returns in approximately 30-40% of patients. The current standard of care includes the use of steroids, calcineurin inhibitors, ACE inhibitors or ARBs, immunosuppressive drugs, diuretics, plasmapheresis, diet change and statins. Only 20% of patients, however, achieve complete remission after 5 years of treatment, and 40% of patients show no remission (Focal and Segmental Glomerulosclerosis: Definition and Relevance of a Partial Remission. Troyanov et al, J Am Soc Nephrol 16: 1061-1068, 2005). There remains, therefore, a need to develop new efficacious drugs to treat the disease.

BRIEF SUMMARY

The present disclosure is directed to methods of treating focal segmental glomerulosclerosis (FSGS) in a patient in need thereof comprising administering to the patient an effective amount of a compound of Formula I:

Formula I or a pharmaceutically acceptable salt thereof,
wherein
$R^1$ is halogen or $C_{1-6}$ alkyl;
$R^2$ is hydrogen, halogen, $C_{1-6}$ alkyl, $C_{1-6}$ alkoxy, $C_{1-6}$ haloalkyl, $C_{1-6}$ haloalkoxy, or —CN;
$R^3$ is hydrogen, halogen, or $C_{1-6}$ alkyl;
$R^4$ is hydrogen, halogen, or $C_{1-6}$ alkyl;
each $R^5$ is independently $C_{1-6}$ alkyl, —OH, or —$NH_2$;
n is 0, 1, 2, or 3; and
each of $A^1$, $A^2$, and $A^3$ is —CH— or —N—, where at least one of $A^1$, $A^2$, or $A^3$ is —N—.

FIGURES

FIG. 1 shows UACR values at baseline, week 1 and week 2 with and without compound 3 treatment in the 5/6 Remnant Kidney Model.

Figure 6:
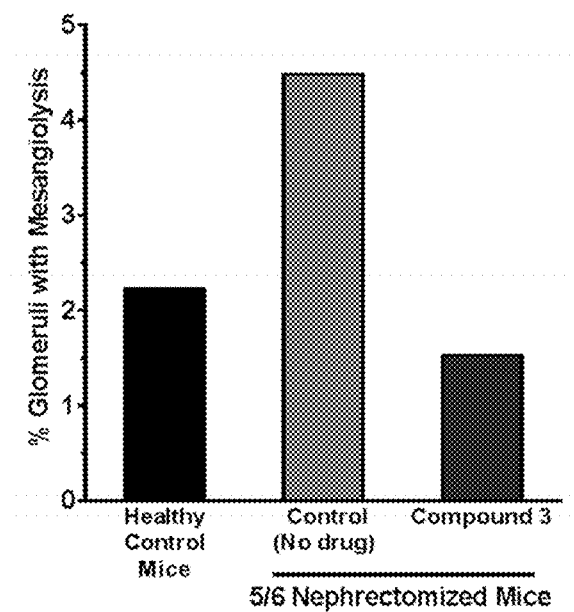

FIG. 6 shows the percentage of glomeruli with mesangiolysis in healthy control mice and 5/6 nephrectomized mice with and without compound 3 treatment in the 5/6 Remnant Kidney Model.

Figure 7:

FIG. 7 shows representative image of glomeruli with mesangiolysis

Figure 8:
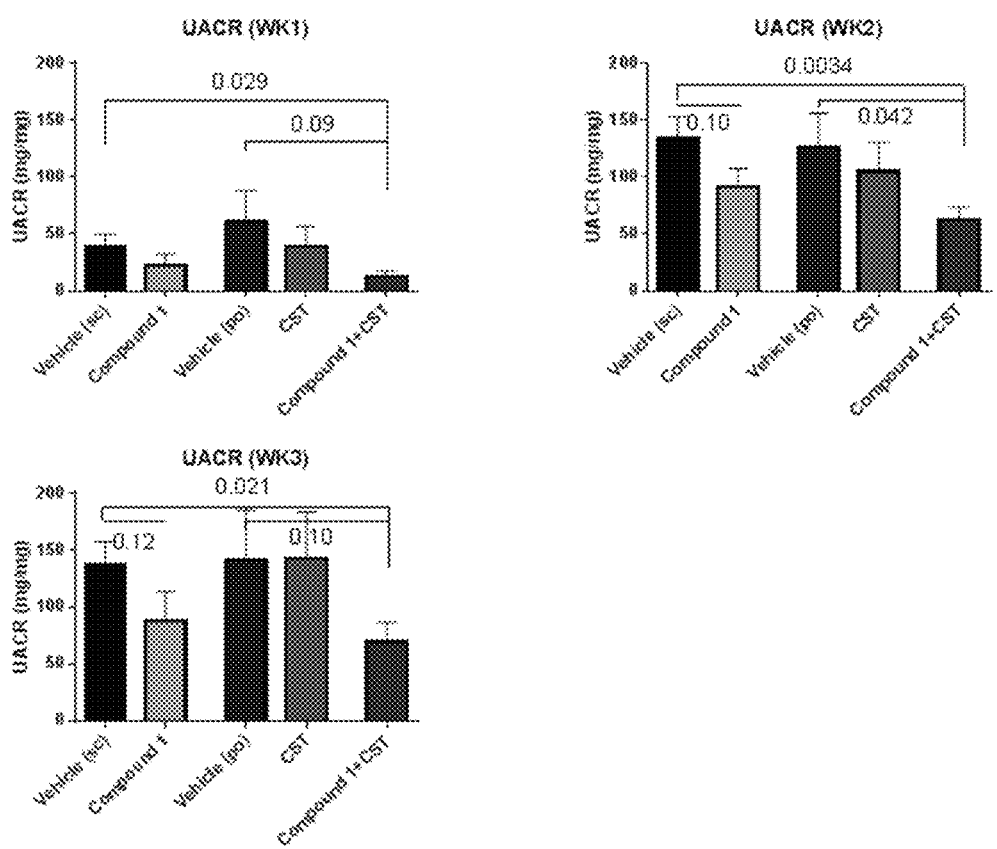

FIG. 8 shows the UACR levels at week 1, 2 and 3 after treatment with compound 1, candesartan and a combination of compound 1 and candesartan compared to vehicles in the Adriamycin nephropathy model.

Figure 9:
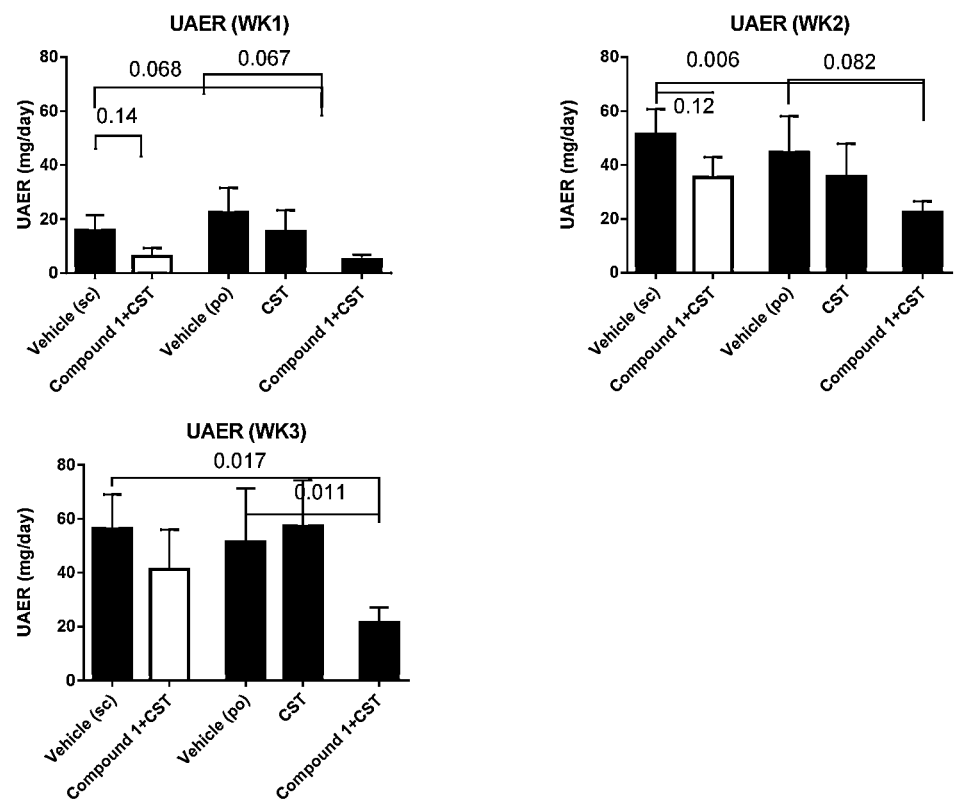

FIG. 9 shows the UAER levels at week 1, 2 and 3 after treatment with compound 1, Candesartan and a combination of compound 1 and candesartan compared to vehicles in the Adriamycin nephropathy model.

Figure 10:
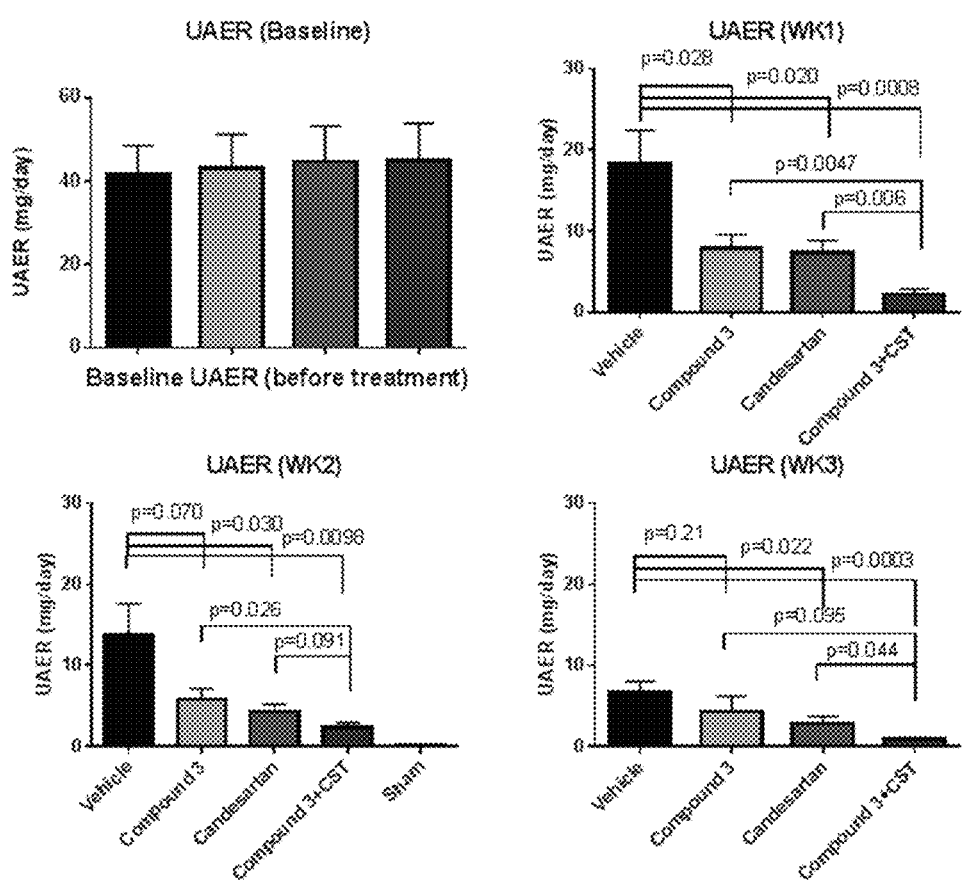

FIG. 10 shows the UAER values at baseline, week 1, 2 and 3 with compound 3 treatment, candesartan treatment and a combination of compound 3 and candesartan treatment in the 5/6 Remnant Kidney Model.

Figure 11:
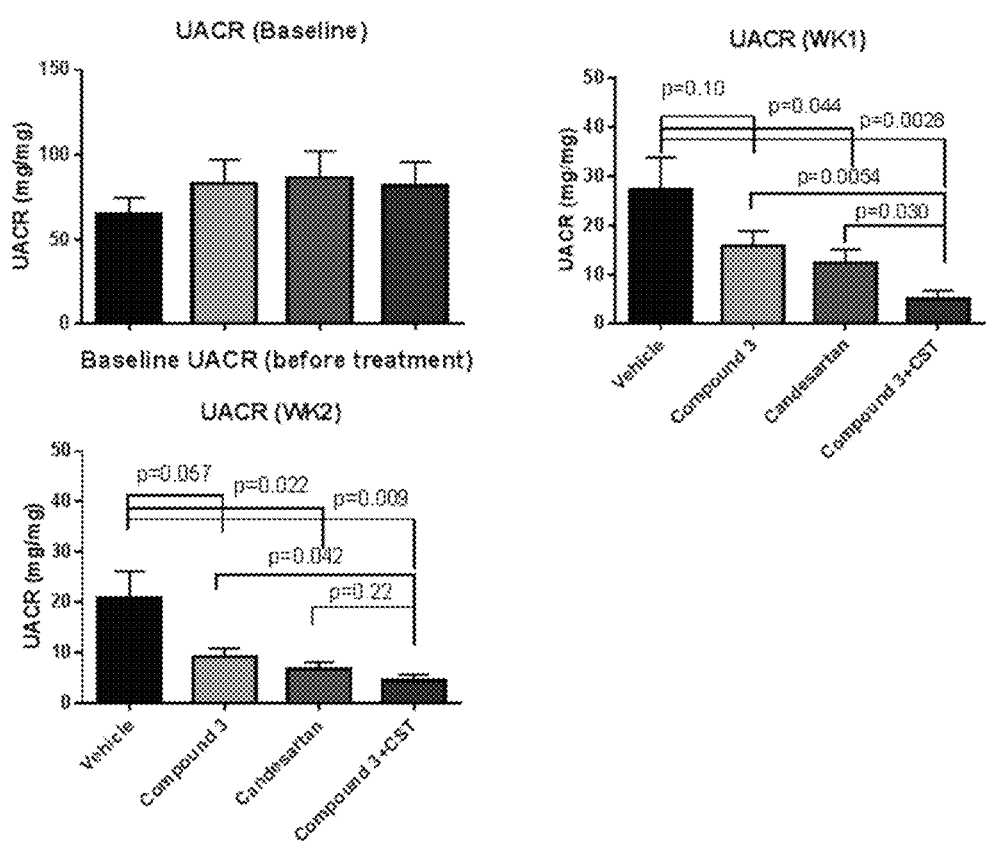

FIG. 11 shows the UACR values at baseline, week 1 and week 2 with compound 3 treatment, candesartan treatment and a combination of compound 3 and candesartan treatment in the 5/6 Remnant Kidney Model.

DETAILED DESCRIPTION

Abbreviations and Definitions

When describing the compounds, compositions, methods and processes of this disclosure, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups are unsubstituted, unless otherwise indicated. Examples of substituted alkyl include haloalkyl, thioalkyl, aminoalkyl, and the like.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred, although alkenyl can have more than 8 carbon atoms. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups are unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups are unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups are unsubstituted, unless otherwise indicated.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups are unsubstituted, unless otherwise indicated. For substituted groups, the substitution may be on a carbon or heteroatom. For example, when the substitution is oxo (=O or —O⁻), the resulting group may have either a carbonyl (—C(O)—) or a N-oxide (—N⁺—O⁻).

Suitable substituents for substituted alkyl, substituted alkenyl, and substituted alkynyl include halogen, —CN, —CO₂R', —C(O)R', —C(O)NR'R", oxo (=O or —O⁻), —OR', —OC(O)R', —OC(O)NR'R"—NO₂, —NR'C(O)R", —NR'''C(O)NR'R", —NR'R", —NR'CO₂R", —NR'S(O)R", —NR'S(O)₂R''', —NR'''S(O)NR'R", —NR'''S(O)₂NR'R", —SR', —S(O)R', —S(O)₂R', —S(O)₂NR'R", —NR'—C(NHR")=NR''', —SiR'R"R''', —N₃, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO$_2$R', —O(O)R', —C(O)NR'R'', oxo (=O or —O$^-$), —OR', —OC(O)R', —OC(O)NR'R'', —NO$_2$, —NR'C(O)R'', —NR'''C(O)NR'R'', —NR'R'', —NR'CO$_2$R'', —NR'S(O)R'', —NR'S(O)$_2$R'', —NR'''S(O)NR'R'', —NR''S(O)$_2$NR'R'', —SR', —S(O)R', —S(O)$_2$R', —S(O)$_2$NR'R'', —NR'—C(NHR'')=NR''', —SiR'R''R''', —N$_3$, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to the total number of open valences on the aromatic ring system.

As used above, R', R'' and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R'' are attached to the same nitrogen atom, they can be combined with the nitrogen atom to form a 3-, 4-, 5-, 6-, or 7-membered ring (for example, —NR'R'' includes 1-pyrrolidinyl and 4-morpholinyl). Furthermore, R' and R'', R'' and R''', or R' and R''' may together with the atom(s) to which they are attached, form a substituted or unsubstituted 5-, 6-, or 7-membered ring.

Two of the substituents on adjacent atoms of an aryl or heteroaryl ring may optionally be replaced with a substituent of the formula -T-(O)—(CH$_2$)$_q$—U—, wherein T and U are independently —NR''''—, O—O—, —CH$_2$— or a single bond, and q is an integer of from 0 to 2. Alternatively, two of the substituents on adjacent atoms of the aryl or heteroaryl ring may optionally be replaced with a substituent of the formula -A'—(CH$_2$)$_r$—B'—, wherein A' and B' are independently —CH$_2$—, —O—, —NR''''—, —S—, —S(O)—, —S(O)$_2$—, —S(O)$_2$NR''''— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR''''—, —S—, —S(O)—, —S(O)$_2$—, or —S(O)$_2$NR'—. R'''' in is selected from hydrogen or unsubstituted C$_{1-8}$ alkyl.

"Heteroatom" is meant to include oxygen (O), nitrogen (N), sulfur (S) and silicon (Si).

"Above natural isotopic abundance" refers to the abundance of isotopes of a chemical element as naturally measured.

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphorsulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition in a patient, such as a mammal (particularly a human or a companion animal) which includes ameliorating the disease or medical condition, i.e., eliminating or causing regression of the disease or medical condition in a patient; suppressing the disease or medical condition, for example slowing or arresting the development of the disease or medical condition in a patient; or alleviating the symptoms of the disease or medical condition in a patient; or preventing the disease to develop.

"UACR" refers to Urine Albumine to Creatinine Ratio.

"UAER" refers to Urinary Albumin Excretion Rate.

Certain compounds of the present disclosure can exist in unsolvated forms as well as solvated forms, including hydrated forms. In general, both solvated forms and unsolvated forms are intended to be encompassed within the scope of the present disclosure.

It will be apparent to one skilled in the art that certain compounds of the present disclosure may exist in tautomeric forms, all such tautomeric forms of the compounds being within the scope of the disclosure. Certain compounds of the present disclosure possess asymmetric carbon atoms (optical centers) or double bonds; the racemates, diastereomers, geometric isomers and individual isomers (for example separate enantiomers) are all intended to be encompassed within the scope of the present disclosure.

The compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. All isotopic variations of the compounds of the present disclosure, whether radioactive or not, are intended to be encompassed within the scope of the present disclosure. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment.

Method of Treating FSGS

The present disclosure provides methods of treating FSGS in a patient comprising administering to the patient in need thereof an effective amount of a compound of Formula (Ia):

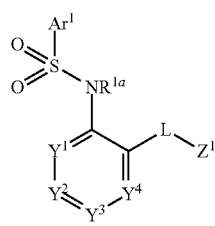

(Ia)

or a pharmaceutically acceptable salt thereof, wherein $Ar^1$ is selected from the group consisting of substituted or unsubstituted $C_{6-10}$ aryl and substituted or unsubstituted 5- to 10-membered heteroaryl;

$R^{1a}$ is selected from the group consisting of hydrogen, substituted or unsubstituted $C_{1-8}$ alkyl, substituted or unsubstituted $C_{2-6}$ alkenyl, substituted or unsubstituted $C_{2-6}$ alkynyl, and substituted or unsubstituted 3- to 10-membered heterocyclyl;

$Y^1$ is selected from the group consisting of —$CR^{2a}$—, —N—, and —$N^+(O)^-$—;

$Y^2$ is selected from the group consisting of —$CR^{2b}$—, —N—, and —$N^+(O)^-$—;

$Y^3$ is selected from the group consisting of —$CR^{2c}$—, —N—, and —$N^+(O)^-$—;

$R^{2a}$, $R^{2b}$, and $R^{2c}$ are each independently selected from the group consisting of hydrogen, halogen, —CN, —C(O)$R^{3a}$, —CO$_2R^{3a}$, —C(O)NR$^{3a}R^{4a}$, —OR$^{3a}$, —OC(O)$R^{3a}$, —OC(O)NR$^{3a}R^{4a}$, —SR$^{3a}$, —S(O)$R^{3a}$, —S(O)$_2R^{3a}$, —S(O)$_2$NR$^{3a}R^{4a}$, —NO$_2$, —NR$^{3a}R^{4a}$, —NR$^{3a}$C(O)$R^{4a}$, —NR$^{3a}$C(O)OR$^{4a}$, —NR$^{3a}$S(O)$_2R^{4a}$, —NR$^{3a}$C(O)NR$^{4a}R^{6a}$, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, and substituted or unsubstituted 5- to 10-membered heteroaryl;

$R^{3a}$, $R^{4a}$, and $R^{5a}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{3a}$ and $R^{4a}$, $R^{4a}$ and $R^{51}$ or $R^{3a}$ and $R^{5a}$ may, together with the atoms to which they are attached, form a substituted or unsubstituted 5-, 6-, or 7-membered ring;

L is selected from the group consisting of a bond, —O—, —S—, —S(O)—, —S(O)$_2$—, —$CR^6R^7$—, —NR$^8$—, —C(O)— and —NR$^8$C(O)—;

$R^6$ and $R^7$ are each independently selected from the group consisting of hydrogen, halogen, substituted or unsubstituted $C_{1-8}$ alkyl, substituted or unsubstituted 3- to 10-membered heterocyclyl, substituted or unsubstituted $C_{2-6}$ alkenyl, substituted or unsubstituted $C_{2-6}$ alkynyl, —CN, —OR$^9$, —NR$^{10}R^{11}$, —S(O)$R^9$, and —S(O)$_2R^9$;

$R^6$ and $R^7$ may, together with the carbon atom to which they are attached, form substituted or unsubstituted $C_{3-8}$ cycloalkyl or substituted or unsubstituted 3- to 10-membered heterocyclic ring;

$R^9$ is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted $C_{6-10}$ aryl, substituted or unsubstituted 5- to 10-membered heteroaryl, and substituted or unsubstituted 3- to 10-membered heterocyclyl;

$R^{10}$ and $R^{11}$ are each independently selected from the group consisting of substituted or unsubstituted $C_{1-8}$ alkyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted $C_{2-8}$ alkenyl, and substituted or unsubstituted $C_{2-8}$ alkynyl;

$R^{10}$ and $R^{11}$ of —NR$^{10}R^{11}$ may, together with the nitrogen, form a substituted or unsubstituted $C_{3-8}$ cycloalkyl or substituted or unsubstituted 3- to 10-membered heterocyclyl;

$R^8$ is selected from the group consisting of hydrogen, $C(O)R^{12}$, $S(O)_2R^{12}$, $CO_2R^{12}$, substituted or unsubstituted $C_{1-8}$ alkyl, substituted or unsubstituted 3- to 10-membered heterocyclyl, substituted or unsubstituted $C_{2-6}$ alkenyl, and substituted or unsubstituted $C_{2-6}$ alkynyl;

$R^{12}$ is selected from the group consisting of substituted or unsubstituted $C_{1-8}$ alkyl, substituted or unsubstituted $C_{2-6}$ alkenyl, substituted or unsubstituted $C_{2-6}$ alkynyl, substituted or unsubstituted 3- to 10-membered heterocyclyl, substituted or unsubstituted $C_{6-10}$ aryl, and substituted or unsubstituted 5- to 10-membered heteroaryl;

$Z^1$ is selected from the group consisting of substituted or unsubstituted $C_{6-10}$ aryl, substituted or unsubstituted 5- to 10-membered heteroaryl, substituted or unsubstituted 3- to 10-membered heterocyclyl, and $-NR^{13}R^{14}$;

$R^{13}$ and $R^{14}$ are each independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted 3- to 10-membered heterocyclyl, substituted or unsubstituted $C_{6-10}$ aryl, substituted or unsubstituted 5- to 10-membered heteroaryl, substituted or unsubstituted ($C_{1-4}$ alkyl)-($C_{6-10}$ aryl), and substituted or unsubstituted ($C_{1-4}$ alkyl)-(5- to 10-membered heteroaryl);

$R^{13}$ and $R^{14}$ may, together with the nitrogen, form a substituted or unsubstituted 4-, 5-, 6-, or 7-membered heterocyclyl;

$Y^4$ is selected from the group consisting of $-N-$ and $-N^+(O)^--$;

In some embodiments, the compounds of formula CC are excluded from formula (Ia):

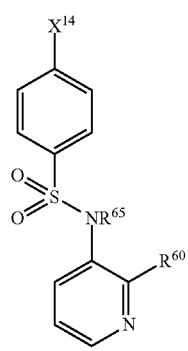

CC where $X^{14}$ is selected from the group consisting of $-Cl$, $-NO_2$, $-OCH_3$, $-CH_3$, $-NHC(O)CH_3$, and $-CH_2CH_2$-(phenyl);

$R^{65}$ is selected from the group consisting of hydrogen, substituted or unsubstituted $C_{1-4}$ alkyl, and substituted or unsubstituted $-SO_2$(phenyl); and $R^{60}$ is selected from the group consisting of $-NR^{61}CH_2CH_2OR^{62}$, $-NR^{61}CH_2CH_2NR^{63}R^{64}$, $-NR^{61}CH_2CH_2SR^{62}$,

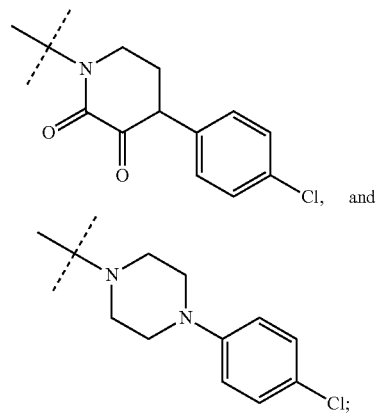

where $R^{61}$ is selected from the group consisting of hydrogen and substituted or unsubstituted phenyl;

$R^{62}$ is selected from the group consisting of substituted or unsubstituted phenyl, and substituted or unsubstituted $C_{1-4}$ alkyl; and $R^{63}$ and $R^{64}$ are each independently selected from the group consisting of hydrogen, substituted or unsubstituted $C_{1-8}$ alkyl, substituted or unsubstituted phenyl, substituted or unsubstituted $-SO_2$(phenyl), $-C(O)CH_3$, $-C(O)C(O)OH$, and $-C(O)_2C(CH_3)_3$.

In some embodiments, $Z^1$ is substituted or unsubstituted 5- to 10-membered heteroaryl.

In some embodiments, L is $-C(O)-$.

In some embodiments, $Y^1$ is $-CR^{2a}-$; $Y^2$ is $-CR^{2b}-$; $Y^3$ is $-CR^{2c}-$; and $R^{2a}$, $R^{2b}$, and $R^{2c}$ are each independently selected from the group consisting of hydrogen, halogen, substituted or unsubstituted $C_{1-8}$ alkyl.

In some embodiments, $R^{1a}$ is selected from the group consisting of hydrogen or substituted or unsubstituted $C_{1-8}$ alkyl.

In some embodiments, $Ar^1$ is substituted or unsubstituted $C_{6-10}$ aryl. In some embodiments, $Ar^1$ is $C_{6-10}$ aryl substituted with 1 to 3 substituents selected from halogen, $C_{1-6}$ alkyl and $C_{1-6}$ haloalkyl. In some embodiments, $Ar^1$ is phenyl substituted with 1 to 3 substituents selected from halogen, $C_{1-3}$ alkyl and $C_{1-3}$ haloalkyl.

In some embodiments, $Y^4$ is $-N-$.

In some embodiments, $Z^1$ is substituted or unsubstituted 5- to 10-membered heteroaryl; L is $-C(O)-$; $Y^1$ is $-CR^{2a}-$; $Y^2$ is $-CR^{2b}-$; $Y^3$ is $-CR^{2c}-$; $R^{2a}$, $R^{2b}$, and $R^{2c}$ are each independently selected from the group consisting of hydrogen, halogen, substituted or unsubstituted $C_{1-8}$ alkyl; $R^{1a}$ is selected from the group consisting of hydrogen or substituted or unsubstituted $C_{1-8}$ alkyl; $Ar^1$ is substituted or unsubstituted $C_{6-10}$ aryl; and $Y^4$ is $-N-$.

In some embodiments, $Z^1$ is unsubstituted 9- to 10-membered heteroaryl; L is $-C(O)-$; $Y^1$ is $-CR^{2a}-$; $Y^2$ is $-CR^{2b}-$; $Y^3$ is $-CR^{2c}-$; $R^{2a}$, $R^{2b}$, and $R^{2c}$ are each independently selected from the group consisting of hydrogen, halogen, and $C_{1-8}$ alkyl; $R^{1a}$ is selected from the group consisting of hydrogen or $C_{1-8}$ alkyl; $Ar^1$ is phenyl substituted with 1 to 3 substituents selected from halogen, $C_{1-6}$ alkyl and $C_{1-6}$ haloalkyl; and $Y^4$ is $-N-$.

The present disclosure also provides methods of treating focal segmental glomerulosclerosis (FSGS) in a patient in need thereof comprising administering to the patient an effective amount of a compound of Formula I:

Formula I or a pharmaceutically acceptable salt thereof, wherein

R¹ is halogen or $C_{1-6}$ alkyl;

R² is hydrogen, halogen, $C_{1-6}$ alkyl, $C_{1-6}$ alkoxy, $C_{1-6}$ haloalkyl, $C_{1-6}$ haloalkoxy, or —CN;

R³ is hydrogen, halogen, or $C_{1-6}$ alkyl;

R⁴ is hydrogen, halogen, or $C_{1-6}$ alkyl;

each R⁵ is independently $C_{1-6}$ alkyl, —OH, or —NH₂;

n is 0, 1, 2, or 3; and each of A¹, A², and A³ is —CH— or —N—, where at least one of A¹, A², or A³ is —N—.

In some embodiments, R¹ is halogen or methyl;

R² is halogen or $C_{1-3}$ haloalkyl;

R³ is halogen or $C_{1-3}$ alkyl;

R⁴ is hydrogen;

n is 0;

A² is —CH—; and

A³ is —N—.

In some embodiments, the compound is:

1 or a pharmaceutically acceptable salt thereof.

In some embodiments, the compound is

2 or a pharmaceutically acceptable salt thereof.

In some embodiments, the compound is

3 or a pharmaceutically acceptable salt thereof.

In some embodiments, the method of treating FSGS comprises preventing, reducing or eliminating a symptom or complication of FSGS.

In some embodiments, the method of treating FSGS comprises preventing, eliminating or delaying the onset of end stage renal disease in the patient.

In some embodiments, the FSGS is primary FSGS.

In some embodiments, the FSGS is secondary FSGS. In some embodiments, the secondary FSGS is associated with an infection or virus, a disease, exposure to a toxin or a drug, or nephron loss and hyperfiltration. In some embodiments, the FSGS is associated with HIV, sickle cell disease, lupus, exposure to an anabolic steroid, heroin or pamidronate, chronic pyelonephritis and reflux, morbid obesity, or diabetes mellitus.

In some embodiments, the method comprises one or more of: decreasing proteinuria, slowing the increase in proteinuria, reducing UACR, slowing the increase in urinary albumin creatinine ratio (UACR), decreasing UAER, slowing the increase in UAER, reducing albuminuria, slowing the increase in albuminuria, increasing glomerular podocyte density, preventing or slowing glomerular basement membrane (GBM) thickening, decreasing glomerular area, reducing the number of renal interstitial macrophages, decreasing or slowing fibrosis of renal tissues, stopping or decreasing inflammation in the kidneys, stopping or decreasing macrophage-induced damage to the kidneys, increasing or normalizing estimated glomerular filtration rate (eGFR), attenuating the decline of eGFR, reducing glomerulosclerosis, stopping or decreasing expansion of the glomerular extracellular matrix, stopping or decreasing deposition of hyaline masses, stopping or reducing glomerular epithelial hyperplasia lesions (EPHLs), and stopping or decreasing lymphocyte infiltration.

In some embodiments, the compound or a pharmaceutically acceptable salt thereof is administered orally.

In some embodiments, the compound or a pharmaceutically acceptable salt thereof is administered twice per day.

In some embodiments, the compound or a pharmaceutically acceptable salt thereof is administered once per day.

In some embodiments, the compound or a pharmaceutically acceptable salt thereof is not administered with any other therapeutic compound. In some embodiments, the compound or a pharmaceutically acceptable salt thereof is not administered with any other therapeutic compound, concurrently or sequentially. In some embodiments, the compound or a pharmaceutically acceptable salt thereof is administered alone. In some embodiments, the compound or a pharmaceutically acceptable salt thereof is not administered with an angiotensin receptor II blocker (ARB). In some embodiments, the compound or a pharmaceutically acceptable salt thereof is not administered with an angiotensin receptor II blocker (ARB), concurrently or sequentially.

In some embodiments, the method further comprises administering to the patient one or more additional therapeutic compound. In some embodiments, the one or more additional therapeutic compound is selected from one or more of an antihypertensive, a statin, a vasodilator, a steroid, a cytotoxic drug, a diuretic, a non-steroidal anti-inflammatory drug (NSAID), a cholesterol or triglycerides reducing agent, and an immunosuppressive drug.

In some embodiments, the one or more additional therapeutic compound is selected from the group consisting of an angiotensin converting enzyme (ACE) inhibitor and an angiotensin receptor II blocker (ARB). In some embodiments, the one or more additional therapeutic compound is selected from the group consisting of ramipril, perindopril, lisinopril, perindopril arginine, captopril, spirapril, quinapril, enalapril, imidapril, fosinopril, zofenopril, benazepril, trandolapril, verapamil, benazepril, amlodipine, trandolapril, P-003, cilazapril, delapril, moexipril, quinapril, fosinopril, temocapril, losartan, candesartan, irbesartan, telmisartan, olmesartan, valsartan, azilsartan, telmisartan, fimasartan, EMA-401, azilsartan medoxomil potassium, sparsentan, candesartan cilexetil, olmesartan medoxomil, TRV-027, losartan potassium, YH-22189, azilsartan trimethylethanolamine, allisartan isoproxil, and eprosartan. In some embodiments, the one or more additional therapeutic compound is candesartan. In some embodiments, the one or more additional therapeutic compound is irbesartan.

In some embodiments, the compound or a pharmaceutically acceptable salt thereof is administered with an angiotensin converting enzyme (ACE) inhibitor, concurrently or sequentially.

In some embodiments, the compound or a pharmaceutically acceptable salt thereof is administered with an angiotensin receptor II blocker (ARB), concurrently or sequentially.

In some embodiments, the one or more additional therapeutic compound is selected from the group consisting of an Endothelin ET-A antagonist, a B-lymphocyte antigen CD20 inhibitor, a sodium glucose transporter-2 inhibitor, a T cell surface glycoprotein CD28 inhibitor; a cytotoxic T-lymphocyte protein-4 stimulator, a 38 MAP kinase inhibitor, a N acetylmannosamine kinase stimulator, an adrenocorticotrophic hormone ligand, an integrin alpha-V/beta-3 antagonist; a connective tissue growth factor ligand inhibitor, and a TGF beta antagonist.

In some embodiments, the one or more additional therapeutic compound is selected from the group consisting of rituximab, dapagliflozin, sparsentan, abatacept, DMX-200, propagermanium, irbesartan, losmapimod, X-M74, Acthar Gel, VAR-200, cilengitide, pamrevlumab, DEX-M74, fresolimumab, and SHP-627.

In some embodiments, the one or more additional therapeutic compound is selected from the group consisting of a farnesoid X receptor agonist, a G-protein coupled bile acid receptor 1 agonist, an Endothelin ET-A antagonist, an Endothelin ET-1 antagonist, an Endothelin ET-2 antagonist, an Endothelin ET-3 antagonist, an Endothelin ET-B1 antagonist, an Endothelin ET-B2 antagonist, an Endothelin ET-C antagonist, a B-lymphocyte stimulator ligand inhibitor, a parathyroid hormone ligand inhibitor, a DNA polymerase inhibitor, a B-lymphocyte antigen CD20 inhibitor, a cytotoxic T-lymphocyte protein-4 stimulator, a T cell surface glycoprotein CD28 inhibitor, a MEKK-5 protein kinase inhibitor, a connective tissue growth factor ligand inhibitor, a mannan-binding lectin serine protease-2 inhibitor, a Syk tyrosine kinase inhibitor, a sodium glucose transporter-2 inhibitor, an erythropoietin receptor agonist, an inosine monophosphate dehydrogenase inhibitor; a PurH purine biosynthesis protein inhibitor, a C5 gene inhibitor, a nucleoside reverse transcriptase inhibitor, a cyclin-dependent kinase-4 inhibitor; a cyclin-dependent kinase-6 inhibitor; a retinoblastoma associated protein modulator, an insulin sensitizer, a Kallikrein 1 modulator, a potassium channel inhibitor, a Raf B protein kinase inhibitor, an adrenocorticotrophic hormone ligand, a complement C1s subcomponent inhibitor, a mineralocorticoid receptor antagonist, a Jak1 tyrosine kinase inhibitor, a Jak tyrosine kinase inhibitor, a Jak2 tyrosine kinase inhibitor, a P2Y12 purinoceptor antagonist, a complement C5 factor inhibitor, a growth hormone receptor antagonist, an aldose reductase inhibitor, a serine protease inhibitor, atrypsin inhibitor, a somatostatin receptor agonist, a NADPH oxidase 1 inhibitor, a NADPH oxidase 4 inhibitor, an ANP agonist, a natriuretic peptide receptor B agonist, an I-kappa B kinase inhibitor, a NFE2L2 gene stimulator, a nuclear factor kappa B inhibitor, a STAT3 gene inhibitor, a vasopressin V2 antagonist, a calcineurin inhibitor, an aldosterone antagonist, a mineralocorticoid receptor antagonist, a tumor necrosis factor ligand 13 inhibitor, a thromboxane A2 antagonist, an epidermal growth factor antagonist, an Erbb2 tyrosine kinase receptor inhibitor, an Erbb3 tyrosine kinase receptor inhibitor, an Erbb4 tyrosine kinase receptor inhibitor, a renin inhibitor, a galectin-3 inhibitor, a mineralocorticoid receptor antagonist, a FGF receptor antagonist, a PDGF receptor antagonist, a TGF beta antagonist, a p38 MAP kinase inhibitor, a myosin stimulator, a beta 2 adrenoceptor agonist, a glucocorticoid agonist, a muscarinic receptor antagonist, an amyloid protein deposition inhibitor, an apolipoprotein gene stimulator, a bromodomain containing protein 4 inhibitor, an hepatocyte growth factor agonist, an advanced glycosylation product receptor antagonist, a GHR gene inhibitor; an IGF1 gene inhibitor, a CACNA2D3 calcium channel subunit modulator, a C-type natriuretic peptide ligand, a dendroaspis natriuretic protein ligand, a heat stable enterotoxin receptor agonist, a natriuretic peptide receptor A agonist, a natriuretic peptide receptor B agonist, a natriuretic peptide receptor C agonist, a bone morphogenetic protein-7 ligand modulator, a cyclooxygenase 1 inhibitor, a vasopressin V1 agonist, a N-acetylmannosamine kinase stimulator, an angiotensin converting enzyme 2 stimulator, a PPAR gamma agonist, a prostanoid receptor antagonist, a thromboxane A2 antagonist, a protein tyrosine phosphatase beta inhibitor, a Tek tyrosine kinase receptor stimulator, a bone morphogenetic protein-7 ligand, a caspase inhibitor, a prostacyclin agonist, an aldose reductase inhibitor, a cyclin-dependent kinase-2 inhibitor, a cyclin-dependent kinase-7 inhibitor, a cyclin-dependent kinase-9 inhibitor, a MCL1 gene inhibitor, a sclerostin inhibitor, a complement C5a receptor antagonist, an immunoglobulin gamma Fc receptor IIB antagonist, a prostacyclin agonist, a p38 MAP kinase inhibitor, an hemoglobin modulator, an alkaline phosphatase stimulator, a NFE2L2 gene modulator, a NFKB gene modulator, a Rho associated protein kinase inhibitor, a CX3CR1 chemokine antagonist, a PDGF receptor beta modulator, an heparin agonist, an elastase stimulator, a growth hormone ligand; a growth hormone receptor agonist, a xanthine oxidase inhibitor, an extracellular matrix protein modulator; a proteoglycan modulator, a mineralocorticoid receptor antagonist, a monocyte chemotactic protein 1 ligand inhibitor, an histone deacetylase inhibitor, an hepatocyte growth factor agonist, an albumin agonist, a membrane copper amine oxidase inhibitor, an integrin alpha-V/beta-3 antagonist, a somatostatin receptor agonist, a cyclin dependent kinase inhibitor, a solute carrier family 12A1 inhibitor, a hepatocyte growth factor ligand modulator, an interferon gamma receptor antagonist, a phenylalanine hydroxylase stimulator, a kidney urea transporter modulator, a factor Xa antagonist, a low molecular weight heparin, a dopamine D1 receptor agonist, a dual inhibitor of angiotensin converting enzyme (ACE) and neutral endopeptidase (EP), a thiazide-like diuretic, a potassium sparing diuretic, a carbonic anhydrase inhibitor, a neutral endopeptidase inhibitor, an aldosterone synthase inhibitor; a renin inhibitor; a calcium channel blocker, a potassium channel activator, a beta-adrenergic blocking drug, an alpha adrenergic blocking drug, a nitrate, a nitric oxide donating compound, a lipid lowering agent, a cholesterol absorption inhibitor, a niacin receptor agonist, a niacin receptor partial agonist, a metabolic altering agent, an alpha glucosidase inhibitor, a dipeptidyl peptidase inhibitor, an ergot alkaloid, and a phosphodiesterase-5 (PDE5) inhibitor.

In some embodiments, the one or more additional therapeutic compound is selected from the group consisting of an Endothelin ET-A antagonist, an Endothelin ET-1 antagonist, an Endothelin ET-2 antagonist, an Endothelin ET-3 antagonist, an Endothelin ET-B1 antagonist, an Endothelin ET-B2 antagonist, an Endothelin ET-C antagonist, a B-lymphocyte stimulator ligand inhibitor, a B-lymphocyte antigen CD20 inhibitor, a cytotoxic T-lymphocyte protein-4 stimulator, a T cell surface glycoprotein CD28 inhibitor, a MEKK-5 protein kinase inhibitor, a connective tissue growth factor ligand inhibitor, a mannan-binding lectin serine protease-2 inhibitor, a Syk tyrosine kinase inhibitor, a sodium glucose transporter-2 inhibitor, an erythropoietin receptor agonist, an inosine monophosphate dehydrogenase inhibitor; a C5 gene inhibitor, an insulin sensitizer, a potassium channel inhibitor, a mineralocorticoid receptor antagonist, a Jak1 tyrosine kinase inhibitor, a Jak tyrosine kinase inhibitor, a Jak2 tyrosine kinase inhibitor, a P2Y12 purinoceptor antagonist, a complement C5 factor inhibitor, a calcineurin inhibitor, an aldosterone antagonist, a mineralocorticoid receptor antagonist, a renin inhibitor, a mineralocorticoid receptor antagonist, a FGF receptor antagonist, a PDGF receptor antagonist, a TGF beta antagonist, a p38 MAP kinase inhibitor, a myosin stimulator, a beta 2 adrenoceptor agonist, a glucocorticoid agonist, a muscarinic receptor antagonist, an apolipoprotein gene stimulator, a cyclooxygenase 1 inhibitor, a vasopressin V1 agonist, an angiotensin converting enzyme 2 stimulator, a PPAR gamma agonist, a prostanoid receptor antagonist, a CX3CR1 chemokine antagonist, a PDGF receptor beta modulator, an heparin agonist, an extracellular matrix protein modulator, a mineralocorticoid receptor antagonist, a dual inhibitor of angiotensin converting enzyme (ACE) and neutral endopeptidase (EP), and a dipeptidyl peptidase inhibitor.

In some embodiments, the one or more additional therapeutic compound is selected from the group consisting of INT-767, belimumab, cinacalcet, rituximab, losartan, abatacept, candesartan, selonsertib, myoinositol hexaphosphate, PBI-4050, OMS-721, fostamatinib, irbesartan, canagliflozin, methoxy polyethylene glycol-epoetin beta, mycophenolate mofetil, ALN-CCS, obinutuzumab, renamezin, palbociclib, bosentan, DM-199, budesonide, amifampridine, amifampridine phosphate, dabrafenib, dapagliflozin, dapagliflozin propanediol, corticotropin, TNT-009, defibrotide, finerenone, baricitinib, ticagrelor, ambrisentan, eculizumab, pegvisomant, epalrestat, camostat mesylate, octreotide, octreotide acetate, GKT-831, ularitide, bardoxolone, bardoxolone methyl, tolvaptan, olmesartan medoxomil, tacrolimus, MT-3995, irbesartan+propagermanium, atacicept, ifetroban, ifetroban sodium, afatinib, atrasentan, TAK-272, AST-120, fimasartan, GR-MD-02, CS-3150, pirfenidone, omecamtiv mecarbil, omecamtiv, beclomethasone, beclomethasone dipropionate, apabetalone, sparsentan, ChronSeal, azeliragon, pamrevlumab, atesidorsen, gabapentin enacarbil, gabapentin, imidapril, cenderitide, BMP-7, GLY-230, recombinant erythropoietin stimulating protein, 2MD, terlipressin, pyridoxamine dihydrochloride, pyridoxamine, DEX-M74, GSK-2586881, SER-150-DN, clazosentan, blisibimod, AKB-9778, eptotermin alfa, benazepril, emricasan, epoprostenol, DW-1029M, bendazac lysine, seliciclib, BPS-804, avacopan, ALLO-ASC-DFU, SM-101, plozalizumab, beraprost sodium, beraprost, losmapimod, PEG-bHb-CO, recombinant human alkaline phosphatase, CXA-10, SAR-407899, B1-655088, BOT-191, sulodexide, vonapanitase, somatropin, topiroxostat, SB-030, SHP-627, KBP-5074, EA-230, emapticap pegol, sodium phenylbutyrate, BB-3, Hemalb, tirilazad, ASP-8232, VPI-2690B, octreotide acetate, EPO-018B, torasemide, rhein, PHN-033, eprosartan, KP-100IT, NCTX, ERC-124, sapropterin, parnaparin sodium, parnaparin, fenoldopam, and Vitamin D.

In some embodiments, the patient is also subjected to extracorporeal blood purification, allogenic transplantation, and/or stem cell therapy.

In some embodiments, the one or more additional therapeutic compound is administered concurrently or sequentially.

In some embodiments, the one or more additional therapeutic compound is administered as a single pharmaceutical composition together with the compound of formula I or (Ia), compound 1, compound 2 or compound 3 or as a separate pharmaceutical composition.

Compounds that Modulate CCR2 Activity

The present disclosure provides compounds that modulate CCR2 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the disclosure include, but are not limited to, the exemplary compounds provided herein and salts thereof.

The compounds of the disclosure are thought to interfere with inappropriate T-cell trafficking by specifically modulating or inhibiting a chemokine receptor function. Compounds useful for treating FSGS contemplated by the disclosure include, but are not limited to the exemplary compounds provided herein and pharmaceutically acceptable salts thereof and the compounds provided in U.S. Pat. No. 8,519,135, US 2006/0173019, US 2014/0031348, U.S. Pat. Nos. 7,622,583, 7,884,110 and 8,093,247 which are hereby incorporated by reference.

In some embodiments, the compounds of the disclosure are selective inhibitors of CCR2.

Compositions

This disclosure contemplates the administration of pharmaceutically acceptable compositions comprising a compound of Formula I, Formula (Ia), compound 1, compound 2 or compound 3 for treating focal segmental glomerulosclerosis (FSGS) in a patient in need thereof. The pharmaceutically acceptable compositions may comprise one or more additional therapeutic compound. The one or more additional therapeutic compound may be selected from compounds having efficacy in treating FSGS or renal diseases.

The pharmaceutically acceptable compositions can be administered to humans and other animals orally, rectally, parenterally, intracisternally, intravaginally, intraperitoneally, topically (as by powders, ointments, or drops), bucally, as an oral or nasal spray, or the like.

Liquid dosage forms for oral administration include, but are not limited to, pharmaceutically acceptable emulsions, microemulsions, solutions, suspensions, syrups and elixirs. In addition to the active compound(s), a liquid dosage form may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be incorporated in an injectable product. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The compounds of the present disclosure or a pharmaceutically acceptable salt thereof may be formulated using nanotechnology. Nanoparticles are attractive for medical purposes based on their unique features, such as their surface to mass ratio being larger than that of other particles, their quantum properties, and their ability to adsorb and carry other compounds. Nanoparticles may have dimensions below 0.1 μm or 100 nm. Alternatively, a pharmaceutical composition may comprise relatively large (size >100 nm) nanoparticles, as needed for loading a sufficient amount of drug onto the particles. In addition, for drug delivery, not only engineered particles may be used as carrier, but also the drug itself may be formulated at a nanoscale, and then function as its own carrier. The composition of the engineered nanoparticles may vary. Source materials may be of biological origin like phospholipids, lipids, lactic acid, dextran, chitosan, or have more chemical characteristics like various polymers, carbon, silica, and metals. Especially in the area of engineered nanoparticles of polymer origin there is a vast area of possibilities for the chemical composition. See, for example, Martins et al., Nanoparticle Drug Delivery Systems: Recent Patents and Applications in Nanomedicine, Recent Patents on Nanomedicine, 2013, 3(2), pp. 1-14.

The compounds of the present disclosure or a pharmaceutically acceptable salt thereof may also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, for example tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the disclosure contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds and compositions of the present disclosure may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present disclosure also contemplates administration of the compounds and compositions of the present disclosure in a depot formulation.

An appropriate dosage level of the compound of Formula (I), Formula (Ia), compound 1, 2, or 3 or a pharmaceutically acceptable salt thereof will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 80.0, 90.0, 100.0, 110.0, 120.0, 130.0, 140.0, 150.0, 160.0, 170.0, 180.0, 190.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. For oral administration, in some embodiments, the compositions are provided in the form of tablets containing 150 mg of the active ingredient. For oral administration, in some embodiments, the compositions are provided in the form of tablets containing 10 mg of the active ingredient. For oral administration, in some embodiments, the compositions are provided in the form of tablets containing 5 mg of the active ingredient. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

The compounds and compositions of the present disclosure can be combined with other compounds and compositions having related utilities to prevent and treat FSGS. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of the compound of the present disclosure to another active ingredient may be varied and will depend upon the effective dose of each ingredient. Generally, an effective dose of each will be used. Thus, for example, when a compound of the present disclosure is combined with a second therapeutic compound the weight ratio of the compound of the present disclosure to the second therapeutic compound will generally range from about 1000:1 to about 1:1000, preferably about 200:1 to about 1:200.

In yet another aspect, the present disclosure provides methods of treating or preventing FSGS by administering to a subject having such a condition or disease a therapeutically effective amount of any compound of the present disclosure. Compounds for use in the present methods include those compounds according to Formula (I), Formula (Ia), compound 1, 2 or 3 or a pharmaceutically acceptable salt thereof, those provided as embodiments, those provided with specific structures herein and the compounds provided in U.S. Pat. No. 8,519,135, US 2006/0173019, US 2014/0031348, U.S. Pat. Nos. 7,622,583, 7,884,110 and 8,093,247 which are hereby incorporated by reference. The compounds can be useful to treat a subject in need of treatment. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "therapeutically effective amount" means the amount of the subject compound that will elicit the biological or medical response of a cell, tissue, system, or animal, such as a human, that is being sought by the researcher, veterinarian, medical doctor or other treatment provider.

In one embodiment, the present disclosure provides methods of treating or preventing FSGS involving administering to a subject an effective amount of the compound or composition of the disclosure, where the administering is oral, parenteral, rectal, transdermal, sublingual, nasal or topical.

CCR2 Modulators

The following examples are offered to illustrate, but not to limit, the present disclosure.

Certain molecules disclosed in this patent can exist in different enantiomeric and diastereomeric forms and all such variants of these compounds are within the scope of the disclosure.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

Additional Combinations

The compounds of the disclosure can be supplied alone or in conjunction with one or more other drugs for treating FSGS.

Examples of therapeutic agents that may be combined with a compound or composition of the present disclosure, either administered separately or in the same pharmaceutical composition, include, but are not limited to: modulators of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX3CR1, ChemR23, C5aR, C5a, and C5, or any combination thereof. In some embodiments, the modulator is an antagonist.

Examples of therapeutic agents that may be combined with a compound or composition of the present disclosure, either administered separately or in the same pharmaceutical composition, include, but are not limited to: CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, and CCX168-M1 or any combination thereof.

Examples of other therapeutic agents that may be combined with a compound or composition of the present disclosure, either administered separately or in the same pharmaceutical compositions, include, but are not limited to: a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, cytokines, vaccines and vaccine adjuvants.

Kits and Packages

The terms "kit" and "pharmaceutical kit" refer to a commercial kit or package comprising, in one or more suitable containers, one or more pharmaceutical compositions and instructions for their use. In one embodiment, kits comprising a compound of Formula (I) or (Ia), or compound 1, 2 or 3, or a pharmaceutically acceptable salt thereof, and instructions for its administration are provided. In one embodiment, kits comprising a compound of Formula (I) or (Ia), or compound 1, 2 or 3, or a pharmaceutically acceptable salt thereof, in combination with one or more (e.g., one, two, three, one or two, or one to three) additional therapeutic agents and instructions for their administration are provided.

In one embodiment, the compounds of this disclosure are formulated into administration units which are packaged in a single packaging. The single packaging encompasses but is not limited to a bottle, a child-resistant bottle, an ampoule, and a tube. In one embodiment, the compounds of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

Other Diseases

The compounds of Formula (I), (Ia), compound 1, compound 2 or compound 3, or a pharmaceutically acceptable salt and/or a prodrug thereof, or compositions thereof, used alone or in combinations, may be useful to treat other diseases. These diseases include but are not limited to chronic kidney disease, diabetic nephropathy, end stage renal disease, glomerular diseases, goodpasture syndrome, glomerulonephritis, glomerulosclerosis, igA nephropathy, membranoproliferative glomerulonephritis, membranous glomerulonephritis, Wegener granulomatosis, vasculitis, Anca-vasculitis, renal failure, renal fibrosis, Bartters disease, nephrocalcinosis, hydronephrosis, pyonephrosis, Hepatorenal syndrome, Hemolytic uremic syndrome, Nephritis, Diabetes insipidus, Nephrogenic diabetes insipidus, Renal insufficiency, Neurogenic diabetes insipidus, Wolfram syndrome, Nephrotic syndrome, Minimal change disease, Perinephritis, Dents disease, Gitelman syndrome, Nephrosclerosis, Renal tubule disease, Hepatorenal syndrome, Azotemia, Uremia, Alport syndrome, Glomerulonephritis, Lupus nephritis, Pyelitis, Pyelonephritis, Pyelocystitis, Glomerulus injury, Polycystic kidney disease, Acquired polycystic kidney disease, Autosomal dominant polycystic kidney disease, Autosomal recessive polycystic kidney disease, abderhalden-Kaufmann-Lignac syndrome (Nephropathic Cystinosis), abdominal Compartment Syndrome, acetaminophen-induced Nephrotoxicity, acute Kidney Failure, acute Kidney Injury, acute Lobar Nephronia, acute Phosphate Nephropathy, acute Tubular Necrosis, adenine phosphoribosyltransferase Deficiency, adenovirus Nephritis, alport Syndrome, amyloidosis, angiomyolipoma, analgesic Nephropathy, antiphospholipid Syndrome, anti-TNF-α Therapy-related Glomerulonephritis, APOL1 Mutations, apparent Mineralocorticoid Excess Syndrome, aristolochic Acid Nephropathy, Chinese Herbal Nephropathy, Balkan Endemic Nephropathy, beeturia, β-Thalassemia Renal Disease, bile Cast Nephropathy, BK Polyoma Virus Nephropathy in the Native Kidney, bladder Sphincter Dyssynergia, bladder Tamponade, border-Crossers' Nephropathy, Bourbon Virus and Acute Kidney Injury, acute Renal Dysfunction, Byetta, C1q Nephropathy, cannabinoid Hyperemesis Acute Renal Failure, cardiorenal syndrome, carfilzomib-Induced Renal Injury, CFHR5 nephropathy, Charcot-Marie-Tooth Disease with Glomerulopathy, cholesterol Emboli, Churg-Strauss syndrome, chyluria, colistin nephrotoxicity, collagenofibrotic Glomerulopathy, collapsing Glomerulopathy, Collapsing Glomerulopathy Related to CMV, congenital Nephrotic Syndrome, conorenal syndrome (Mainzer-Saldino Syndrome or Saldino-Mainzer Disease), contrast Nephropathy, copper Sulfate Intoxication, cortical Necrosis, crizotinib-related Acute Kidney Injury, cryoglobuinemia, crystalglobulin-Induced Nephropathy, cystic Kidney Disease, acquired Cystinuria, dense deposit disease, dialysis Disequilibrium Syndrome, diabetic Kidney Disease, diffuse Mesangial Sclerosis, duplicated Ureter, EAST syndrome, Erdheim-Chester Disease, Fabry's Disease, familial Hypocalciuric Hypercalcemia, Fanconi Syndrome, Fraser syndrome, Fibronectin Glomerulopathy, fibrillary Glomerulonephritis and Immunotactoid Glomerulopathy, Fraley syndrome, focal Sclerosis, focal Glomerulosclerosis, Galloway Mowat syndrome, giant cell (Temporal) Arteritis with Kidney Involvement, glomerular Tubular Reflux, glycosuria, hantavirus Infection Podocytopathy, heat Stress Nephropathy, hematuria, atypical Hemolytic Uremic Syndrome (aHUS), hemophagocytic Syndrome, hemorrhagic Cystitis, nephropathis Epidemica, hemosiderinuria, hemosiderosis, glomerulopathy, hepatic glomerulopathy, hepatic veno-occlusive disease, sinusoidal Obstruction Syndrome, hepatitis C-Associated Renal Disease, hepatorenal Syndrome, HIV-Associated Nephropathy (HIVAN), HNF1B-related Autosomal Dominant Tubulointerstitial Kidney Disease, horseshoe Kidney (Renal Fusion), Hunner's Ulcer, hyperaldosteronism, hypercalcemia, hyperkalemia, hypermagnesemia, hypernatremia, hyperoxaluria, hyperphosphatemia, hypocalcemia, hypocomplementemic urticarial Vasculitic Syndrome, hypokalemia, Hypokalemia-induced renal dysfunction, hypokalemic Periodic Paralysis, hypomagnesemia, hyponatremia, hypophosphatemia, IgA Nephropathy, IgG4 Nephropathy, immune-Checkpoint Therapy-Related Interstitial Nephritis, interstitial Cystitis, Painful Bladder Syndrome, interstitial Nephritis, Ivemark's syndrome, Ketamine-Associated Bladder Dysfunction, Kidney Stones, Nephrolithiasis, Kombucha Tea Toxicity, Lead Nephropathy and Lead-Related Nephrotoxicity, Leptospirosis Renal Disease, Light Chain Deposition Disease, Monoclonal Immunoglobulin Deposition Disease, Liddle Syndrome, Lightwood-Albright Syndrome, Lipoprotein Glomerulopathy, Lithium Nephrotoxicity, LMX1B Mutations Cause Hereditary FSGS, Loin Pain Hematuria, Lupus, Systemic Lupus Erythematosus, Lupus Kidney Disease, Lupus Nephritis, Lupus Nephritis with Antineutrophil Cytoplasmic Antibody Seropositivity, Lupus Podocytopathy, Lyme Disease-Associated Glomerulonephritis, Lysozyme Nephropathy, Malarial Nephropathy, Malignancy-Associated Renal Disease, Malignant Hypertension, Malakoplakia, Meatal Stenosis, Medullary Cystic Kidney Disease, Urolodulin-Associated Nephropathy, Juvenile Hyperuricemic Nephropathy Type 1, Medullary Sponge Kidney, Megaureter, Melamine Toxicity and the Kidney, Membranoproliferative Glomerulonephritis, membranous Nephropathy, Membranous-like Glomerulopathy with Masked IgG Kappa Deposits, mesoAmerican Nephropathy, Metabolic Acidosis, Metabolic Alkalosis, Methotrexate-related Renal Failure, Microscopic Polyangiitis, Milk-alkalai syndrome, Minimal Change Disease, MDMA (Molly; Ecstacy; 3,4-Methylenedioxymethamphetamine) and Kidney Failure, MUC1 Nephropathy, Multicystic dysplastic kidney, Multiple Myeloma, Myeloproliferative Neoplasms and Glomerulopathy, Nail-patella Syndrome, Nephrocalcinosis, Nephrogenic Systemic Fibrosis, Nephroptosis (Floating Kidney, Renal Ptosis), Nephrotic Syndrome, Neurogenic Bladder, nodular Glomerulosclerosis, non-Gonococcal Urethritis, nutcracker syndrome, oligomeganephronia, orofaciodigital Syndrome, orotic Aciduria, orthostatic Hypotension, orthostatic Proteinuria, osmotic Diuresis, osmotic Nephrosis, ovarian Hyperstimulation Syndrome, oxalate Nephropathy, page Kidney, papillary Necrosis, papillorenal Syndrome (Renal-Coloboma Syndrome, Isolated Renal Hypoplasia), peritoneal-Renal Syndrome, posterior Urethral Valve, post-infectious Glomerulonephritis, Post-streptococcal Glomerulonephritis, polyarteritis Nodosa, polycystic Kidney Disease, posterior Urethral Valves, preeclampsia, Propofol infusion syndrome, proliferative Glomerulonephritis with Monoclonal IgG Deposits (Nasr Disease), propolis related Renal Failure, proteinuria, pseudohyperaldosteronism, pseudohypobicarbonatemia, pseudohypoparathyroidism, pulmonary-Renal Syndrome, pyelonephritis, pyonephrosis, radiation Nephropathy, refeeding syndrome, reflux Nephropathy, rapidly Progressive Glomerulonephritis, renal Abscess, Peripnephric Abscess, renal Agenesis, renal Arcuate Vein Microthrombi-Associated Acute Kidney Injury, renal Artery Aneurysm, renal Artery Stenosis, renal Cell Cancer, renal Cyst, renal Hypouricemia with Exercise-induced Acute Renal Failure, renal Infarction, renal Osteodystrophy, renal Tubular Acidosis, renin Mutations and Autosomal Dominant Tubulointerstitial Kidney Disease, renin Secreting Tumors (Juxtaglomerular Cell Tumor), reset Osmostat, retrocaval Ureter, retroperitoneal Fibrosis, rhabdomyolysis, Rhabdomyolysis related to Bariatric Surgery, rheumatoid Arthritis-Associated Renal Disease, sarcoidosis Renal Disease, salt Wasting, schistosomiasis and Glomerular Disease, schimke immuno-osseous dysplasia, scleroderma Renal Crisis, serpentine Fibula-Polycystic Kidney Syndrome, Exner Syndrome, sickle Cell Nephropathy, Sjögren's Syndrome, synthetic Cannabinoid Use and Acute Kidney Injury, kidney Disease Following Hematopoietic Cell Transplantation, Kidney Disease Related to Stem Cell Transplantation, Thin Basement Membrane Disease, Benign Familial Hematuria, Trigonitis, Tuberculosis, Tuberous Sclerosis, Tubular Dysgenesis, immune Complex Tubulointerstitial Nephritis Due to Autoantibodies to the Proximal Tubule Brush Border, tumor Lysis Syndrome, uremia, uremic Optic, neuropathy, ureteritis Cystica, ureterocele, urethral Caruncle, urethral Stricture, urinary Incontinence, urinary Tract Infection, urinary Tract Obstruction, uromodulin-Associated Kidney Disease, vasomotor Nephropathy, vesicointestinal Fistula, vesicoureteral Reflux, Von Hippel-Lindau Disease, Waldenstrom's Macroglobulinemic Glomerulonephritis, Warfarin-Related Nephropathy, Wegener's Granulomatosis, Granulomatosis with Polyangiitis, West Nile Virus, Wunderlich syndrome, Zellweger Syndrome, cerebrohepatorenal Syndrome, melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma. For any of these diseases, the compounds of the disclosure may be combined with other therapeutic agents, including the ones disclosed in this disclosure.

EXAMPLES

The remnant kidney and the adryamicin drug-induced models are commonly used rodent models for FSGS (de Mik S M. Et al. Pathophysiology and treatment of focal segmental glomerulosclerosis: the role of animal models. BMC Nephrol. 2013 Apr. 1; 14:74). The 5/6 remnant kidney model is representative of secondary FSGS whereas the Adriamycin nephropathy model is representative of primary FSGS.

Example 1: 5/6 Remnant Kidney Model

The 5/6 remnant kidney 129X1/SvJ mice was obtained from Jackson Laboratories. The mice were kept on standard chow and had free access to water. The mice surgery was performed in two stages. Under isoflurane anesthesia, two-thirds of the left kidney mass was dissected. After 7 to 10 days, a right unilateral nephrectomy was performed. Six weeks after the 5/6 nephrectomy, the mice were randomized for the study. Compound 3 and its vehicle were dosed subcutaneously once daily at 100 mg/kg formulated in 1% HPMC. 6 animals were used for each group.

Urine samples were collected at weeks one and two by individually housing the mice in metabolic cages for 18 hours. Urinary albumin was measured by ELISA (Bethyl Labs, Montgomery, TX), and the urinary albumin excretion rate (UAER) was calculated as micrograms per 24 hours. Urinary creatinine was measured by mass spectrometry. The albumin to creatinine ratio (ACR) was calculated as micrograms of albumin per milligram of creatinine. At the end of the experiments (after 2 weeks of treatment), the kidneys were collected, fixed in formalin, embedded in paraffin, and cut into 3-μm-thick sections. Sections were stained for podocytes by immunohistochemistry with Wilms tumor protein 1 antibody (Abcam, Cambridge, MA). Glomerular cross-sectional area and podocyte number were determined in 20-30 glomeruli per mouse. Glomerulus volume and podocyte density were calculated from the immunohistochemistry data using the Weibel method. Mesangial expansion was measured by silver methenamine stain on 2-μm-thick paraffin sections by conventional methods.

Figure 1:
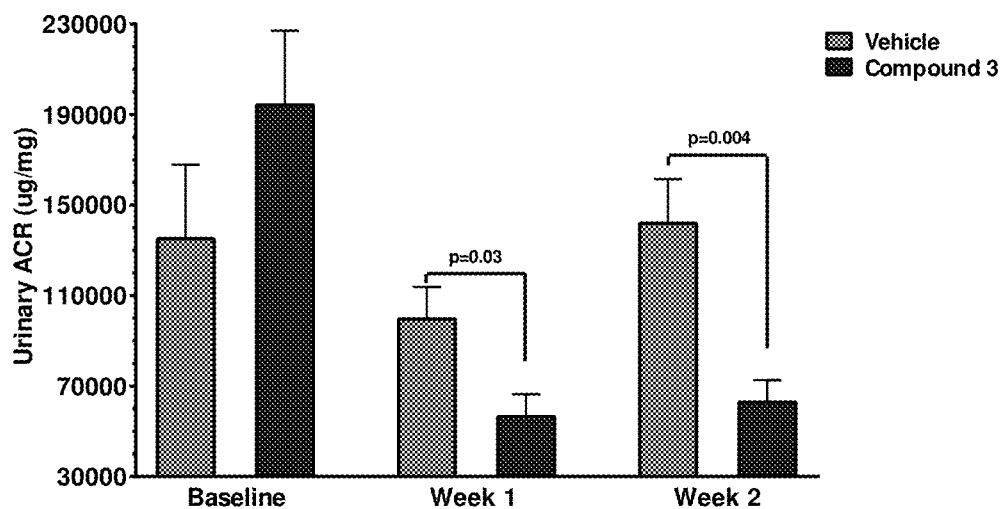

FIG. 1 shows that compound 3 reduces the profound proteinuria in 5/6 Remnant Kidney Model at week 1 and 2.

Figure 2:
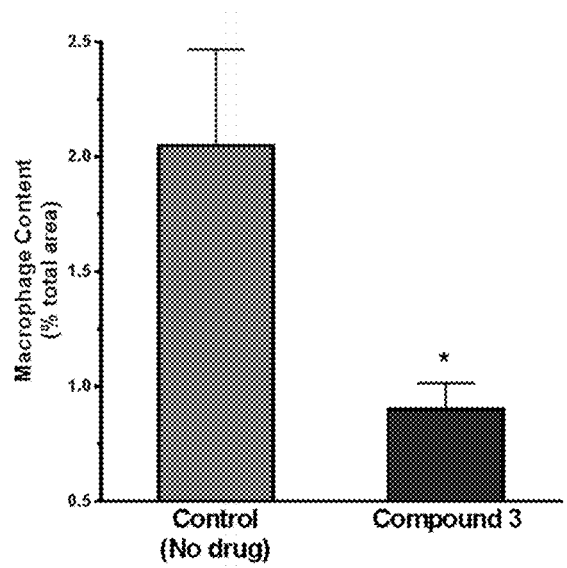
FIG. 2 shows the macrophage content as a percentage of total area with and without compound 3 treatment in the 5/6 Remnant Kidney Model.

FIG. 2 shows that compound 3 reduces the number of renal interstitial macrophages in the 5/6 Remnant Kidney Model.

Figure 3:
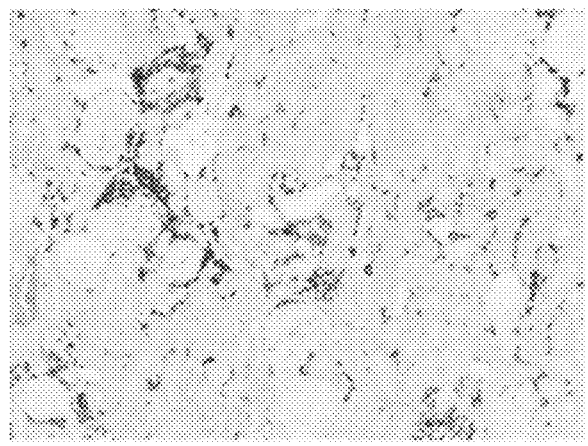
FIG. 3 shows representative images of renal interstitial macrophages in the 5/6 Remnant Kidney Model with and without compound 3 treatment.
Figure 3:
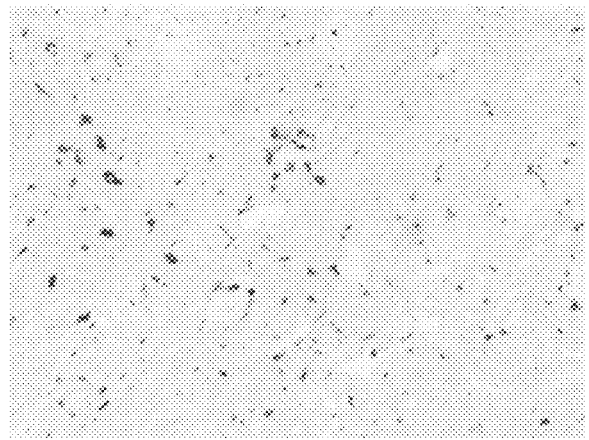

FIG. 3 shows some representative images of renal interstitial macrophages in the 5/6 Remnant Kidney Model with and without compound 3 treatment.

Figure 4:
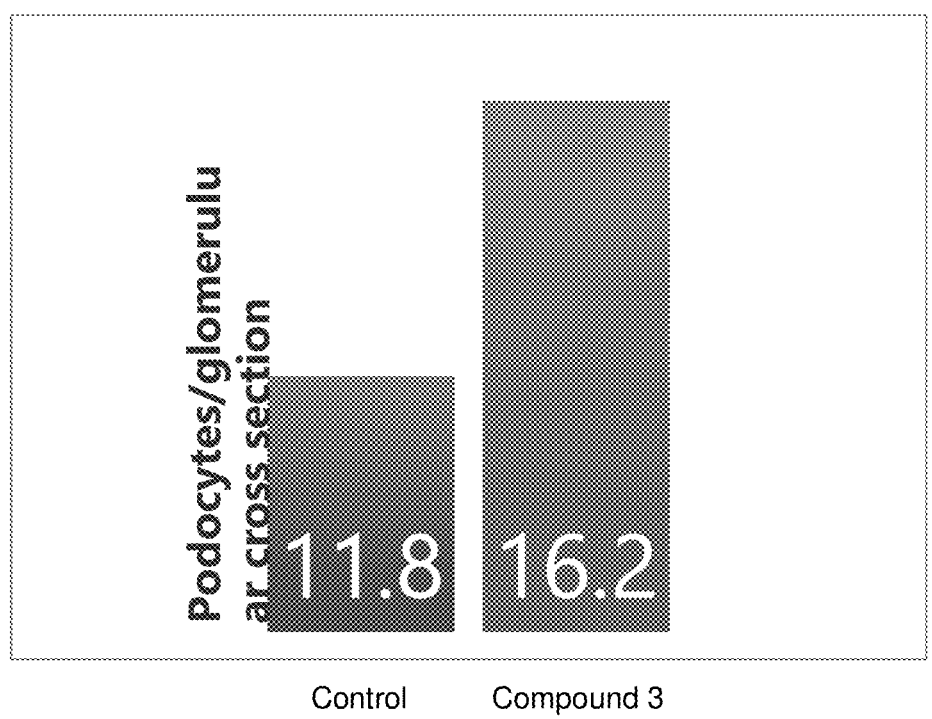
FIG. 4 shows podocytes numbers per glomerular cross section with and without compound 3 treatment in the 5/6 Remnant Kidney Model.

FIG. 4 shows that compound 3 increased podocytes numbers in the 5/6 Remnant Kidney Model.

Figure 5:
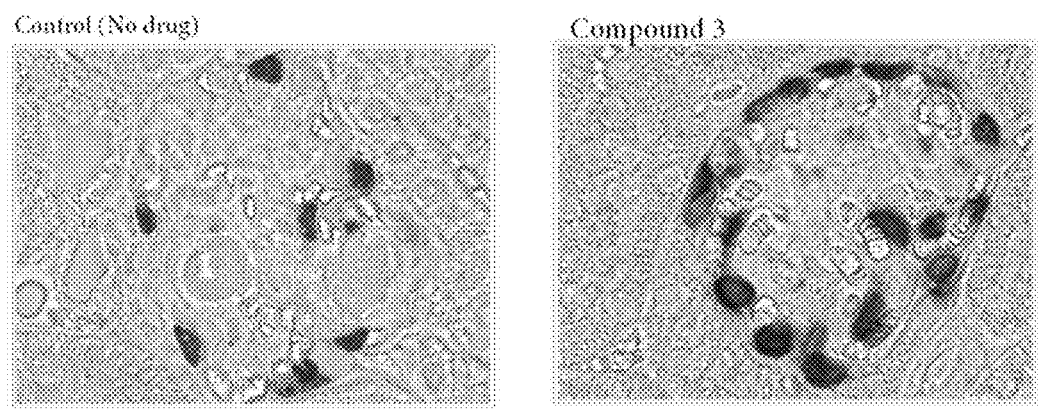
FIG. 5 shows representative images of podocytes in the 5/6 Remnant Kidney Model with and without compound 3 treatment.

FIG. 5 shows representative images of podocytes in the 5/6 Remnant Kidney Model with and without compound 3 treatment.

FIG. 6 shows that compound 3 has a beneficial effect on the percentage of glomeruli with mesangiolysis in 5/6 Remnant Kidney Model.

FIG. 7 shows a representative image of glomeruli with mesangiolysis.

Example 2: Adriamycin Nephropathy Model

The experiment was performed in female Balb/c mice (Jackson Laboratories). The mice were kept on standard chow and had free access to water. 7.5 mg/kg Adriamycin (Selleck Chemicals) or saline (control) was injected in a tail vein in isoflurane-anesthetized animals at day 0. Compound 1 and its vehicle (1% HPMC) were dosed subcutaneously once daily at 90 mg/kg formulated in 1% HPMC. Candesartan and its vehicle (H$_2$O) were dosed orally once daily. Twelve animals were used for each group.

Urine samples were collect at week one and two by individually housing mice in metabolic cages for 18 h. Urinary albumin was measured by ELISA (Bethyl Labs, Montgomery, TX), and the urinary albumin excretion rate (UAER) was calculated as micrograms per 24 hours. Urinary creatinine was measured by mass spectrometry. The albumin to creatinine ratio (ACR) was calculated as micrograms of albumin per milligram of creatinine.

FIG. 8 shows that compound 1 as single agent and in combination with candesartan (CST) leads to reduction in UACR levels.

FIG. 9 shows that compound 1 in combination with candesartan (CST) leads to reduction in UAER levels.

Example 3: 5/6 Remnant Kidney Model with Combination Treatment

The 5/6 remnant kidney 129X1/SvJ mice was obtained from Jackson Laboratories. The mice were kept on standard chow and had free access to water. The mice surgery was performed in two stages. Under isoflurane anesthesia, two-thirds of the left kidney mass was dissected. After seven to ten days, a right unilateral nephrectomy was performed. Three to six weeks after the 5/6 nephrectomy, the mice were randomized for the study (n=12 per group). Compound 3 and its vehicle were dosed subcutaneously once daily at 100 mg/kg formulated in 1% HPMC. Candesartan (AK Scientific) and its vehicle (H$_2$O) were dosed once daily orally at 5 mg/kg. Two animals per group were euthanized at weeks 1, 2, and 3 to perform histology and IHC.

Urine samples were collected at week one, two and three by individually housing the mice in metabolic cages for 18 hours. Urinary albumin was measured by ELISA (Bethyl Labs, Montgomery, TX), and the urinary albumin excretion rate (UAER) was calculated as micrograms per 24 hours. Urinary creatinine was measured by mass spectrometry. The albumin to creatinine ratio (ACR) was calculated as micrograms of albumin per milligram of creatinine.

FIG. 10 shows a reduction in UAER values at weeks 1, 2 and 3 with treatment with compound 3 alone, with treatment with candesartan alone, as well as with treatment with a combination of compound 3 and candesartan in the 5/6 Remnant Kidney Model.

FIG. 11 shows a reduction in UACR values at week 1 and week 2 with treatment with compound 3 alone, with treatment with candesartan alone as well as with treatment with a combination of compound 3 and candesartan in the 5/6 Remnant Kidney Model.

Compound 1 is:

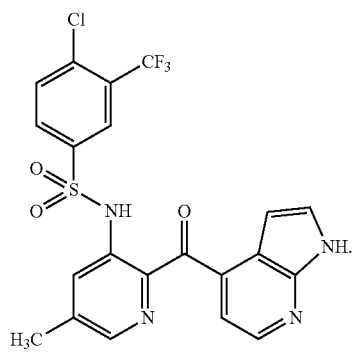 [SMILES: Cc1cnc(C(=O)c2ccnc3[nH]ccc23)c(NS(=O)(=O)c2ccc(Cl)c(C(F)(F)F)c2)c1]

Compound 2 is:

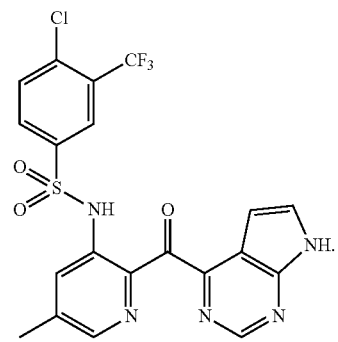

Compound 3 is:

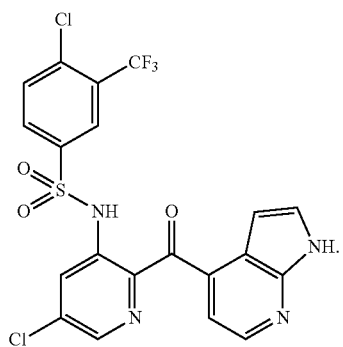

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

The invention claimed is:

1. A method of treating nephritis, wherein the nephritis is adenovirus nephritis, anti-TNF-α Therapy-related glomerulonephritis, fibrillary glomerulonephritis, post-infectious glomerulonephritis, post-streptococcal Glomerulonephritis, Nasr Disease, and rapidly progressive glomerulonephritis in a patient in need thereof, comprising administering to the patient an effective amount of a compound of Formula I:

Formula I

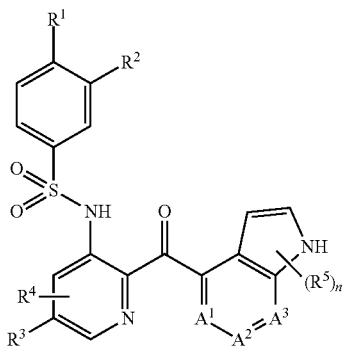

or a pharmaceutically acceptable salt thereof, wherein $R^1$ is halogen or $C_{1-6}$ alkyl;

$R^2$ is hydrogen, halogen, $C_{1-6}$ alkyl, $C_{1-6}$ alkoxy, $C_{1-6}$ haloalkyl, $C_{1-6}$ haloalkoxy, or —CN;

$R^3$ is hydrogen, halogen, or $C_{1-6}$ alkyl;

$R^4$ is hydrogen, halogen, or $C_{1-6}$ alkyl;

each $R^5$ is independently $C_{1-6}$ alkyl, —OH, or —NH$_2$;

n is 0, 1, 2, or 3; and each of $A^1$, $A^2$, and $A^3$ is —CH— or —N—, where at least one of $A^1$, $A^2$, or $A^3$ is —N—.

2. The method of claim 1 wherein $R^1$ is halogen or methyl;

$R^2$ is halogen or $C_{1-3}$ haloalkyl;

$R^3$ is halogen or $C_{1-3}$ alkyl;

$R^4$ is hydrogen;

n is 0;

$A^2$ is —CH—; and $A^3$ is —N—.

3. The method of claim 1, wherein the compound is:

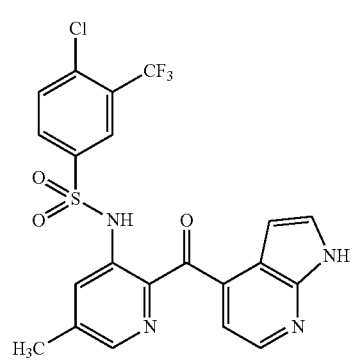

or a pharmaceutically acceptable salt thereof.

4. The method of claim 1, wherein the compound is

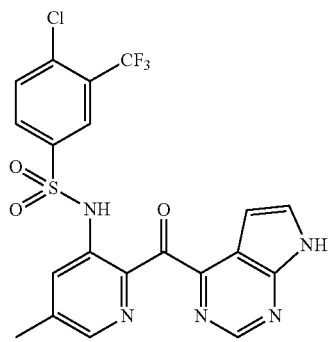

or a pharmaceutically acceptable salt thereof.

5. The method of claim 1, wherein the compound is

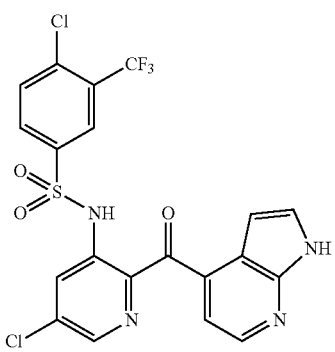

or a pharmaceutically acceptable salt thereof.

6. The method of claim 1, wherein the compound or a pharmaceutically acceptable salt thereof is administered orally.

7. The method of claim 1, wherein the compound or a pharmaceutically acceptable salt thereof is administered twice per day.

8. The method of claim 1, wherein the compound or a pharmaceutically acceptable salt thereof is administered once per day.

9. The method of claim 1, further comprising administering to the patient one or more additional therapeutic compound.

10. The method of claim 9 wherein the one or more additional therapeutic compound is selected from one or more of an antihypertensive, a statin, a vasodilator, a steroid, a cytotoxic drug, a diuretic, a non-steroidal anti-inflammatory drug (NSAID), a cholesterol or triglycerides reducing agent, and an immunosuppressive drug.

11. The method of claim 9 wherein the one or more additional therapeutic compound is selected from the group consisting of an angiotensin converting enzyme (ACE) inhibitor and an angiotensin receptor II blocker (ARB).

12. The method of claim 11 wherein the one or more additional therapeutic compound is selected from the group consisting of ramipril, perindopril, lisinopril, perindopril arginine, captopril, spirapril, quinapril, enalapril, imidapril, fosinopril, zofenopril, benazepril, trandolapril, verapamil, benazepril, amlodipine, trandolapril, P-003, cilazapril, delapril, moexipril, quinapril, fosinopril, temocapril, losartan, candesartan, irbesartan, telmisartan, olmesartan, valsartan, azilsartan, telmisartan, fimasartan, EMA-401, azilsartan medoxomil potassium, sparsentan, candesartan cilexetil, olmesartan medoxomil, TRV-027, losartan potassium, YH-22189, azilsartan trimethylethanolamine, allisartan isoproxil, and eprosartan.

13. The method of claim 1, wherein the patient is also subjected to extracorporeal blood purification, allogenic transplantation, and/or stem cell therapy.

14. The method of claim 9, wherein the one or more additional therapeutic compound is administered concurrently or sequentially.

15. The method of claim 9, wherein the one or more additional therapeutic compound is administered as a single pharmaceutical composition together with the compound of formula I or as a separate pharmaceutical composition.

16. The method of claim 1, wherein the effective amount of the compound of Formula I is 5 mg administered twice daily.

17. The method of claim 1, wherein the effective amount of the compound of Formula I is 10 mg administered twice daily.

18. The method of claim 1, wherein the effective amount of the compound of Formula I is 15 mg administered twice daily.

19. The method of claim 1, wherein the effective amount of the compound of Formula I is 10 mg administered once daily.

20. The method of claim 1, wherein the effective amount of the compound of Formula I is 15 mg administered once daily.

* * * * *